United States Patent [19]
Kikuchi et al.

[11] Patent Number: 5,031,036
[45] Date of Patent: Jul. 9, 1991

[54] ELECTRONIC ENDOSCOPE APPARATUS SIMULTANEOUSLY DISPLAYING AN ORIGINAL PICTURE IMAGE AND SPECIAL PICTURE IMAGE ON A SINGLE DISPLAYING PICTURE SURFACE

[75] Inventors: Kenichi Kikuchi; Kazunari Nakamura, both of Hachioji, Japan

[73] Assignee: Olympus Optical Co., Ltd., Tokyo, Japan

[21] Appl. No.: 375,239

[22] Filed: Jul. 3, 1989

[30] Foreign Application Priority Data

Jul. 11, 1988 [JP] Japan .................................. 63-172265
Jun. 5, 1989 [JP] Japan .................................. 1-143655

[51] Int. Cl.⁵ .......................... A61B 1/04; H04N 9/74; H04N 7/18
[52] U.S. Cl. ........................................ 358/98; 358/22; 358/28
[58] Field of Search ................... 358/98, 183, 22, 111, 358/110, 93, 81, 160, 27, 40, 28; 128/6

[56] References Cited

U.S. PATENT DOCUMENTS

| | | | |
|---|---|---|---|
| 4,665,438 | 5/1987 | Miron et al. | 358/22 X |
| 4,712,133 | 12/1987 | Kikuchi . | |
| 4,768,093 | 8/1988 | Prodan | 358/22 X |
| 4,799,104 | 1/1989 | Hosoya et al. | 358/98 |
| 4,853,773 | 8/1989 | Hibino et al. | 358/98 |
| 4,855,812 | 8/1989 | Rokuda et al. | 358/22 |
| 4,885,634 | 12/1989 | Yabe | 358/98 |

Primary Examiner—Victor R. Kostak
Attorney, Agent, or Firm—Armstrong, Nikaido, Marmelstein, Kubovcik & Murray

[57] ABSTRACT

For a picture image signal imaged by an imaging device, a first signal processing circuit displays an original picture image/contracted original picture image and a second signal processing circuit makes a special picture image processed as an outline enhancement, differentiation and color enhancement are provided. Both picture image signals processed by both circuits are mixed and displayed on the same displaying picture surface.

46 Claims, 23 Drawing Sheets

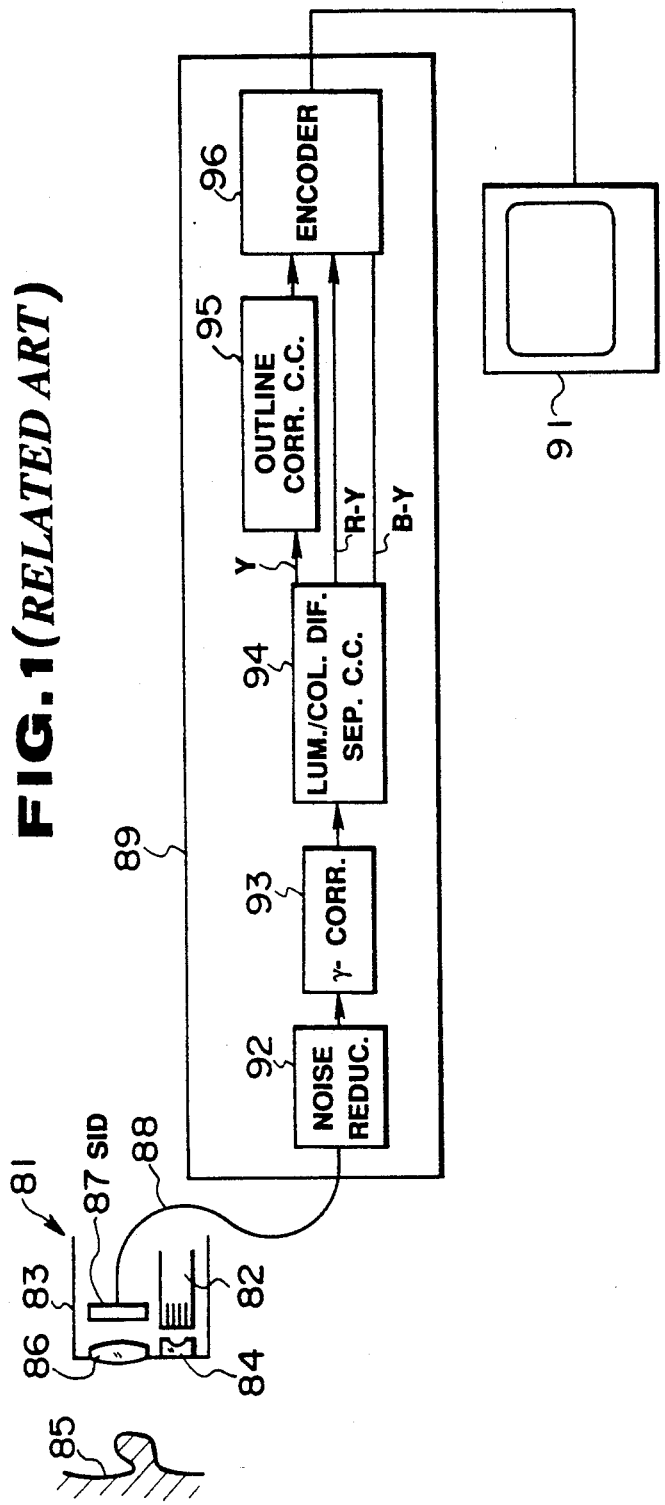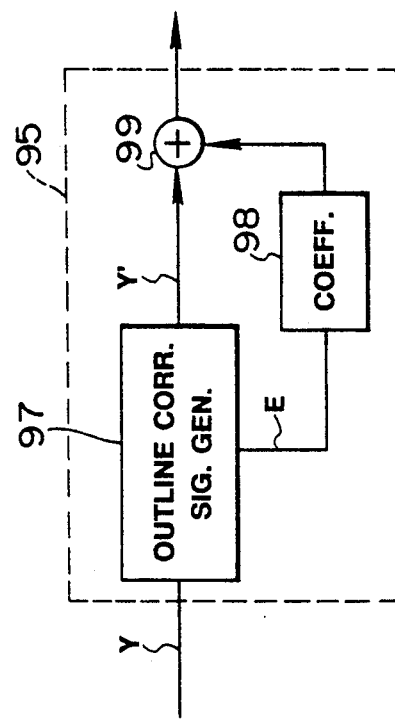

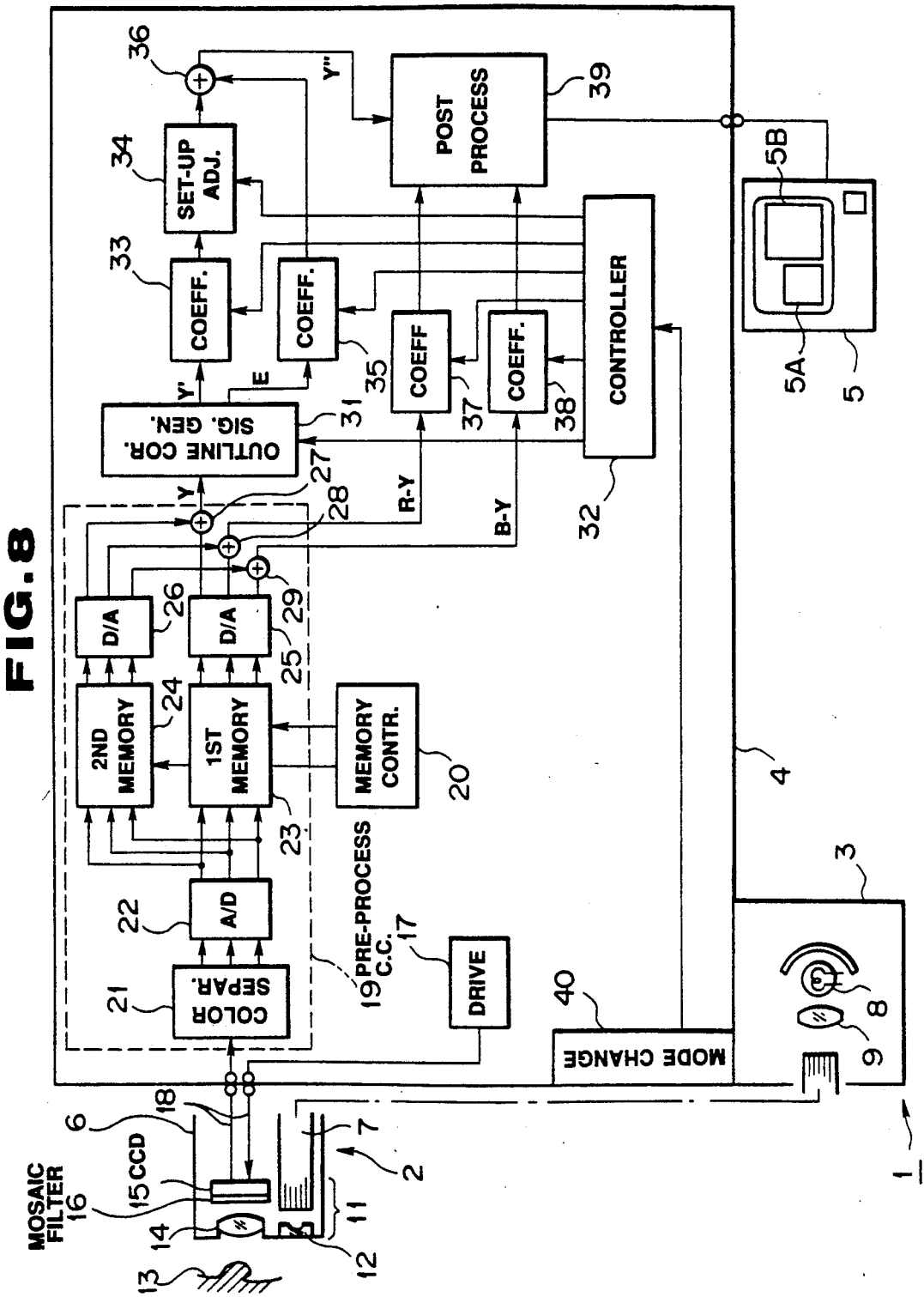

(PRIOR ART)
FIG. 5a Y
FIG. 5b E
FIG. 5c Y'
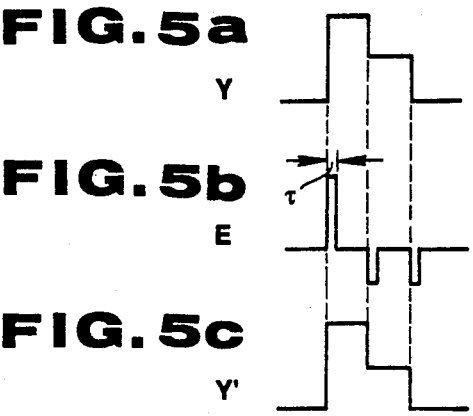
(PRIOR ART)
FIG. 6a Y
FIG. 6b E
FIG. 6c Y'
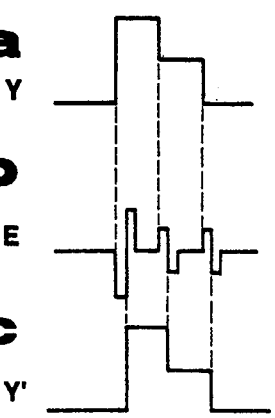
(PRIOR ART)
FIG. 7a
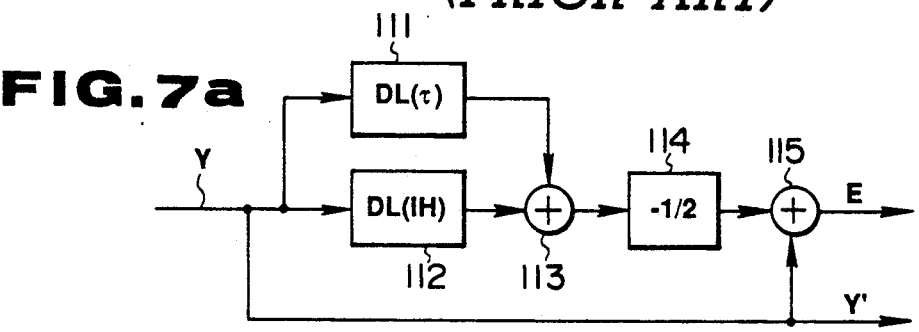
FIG. 7b
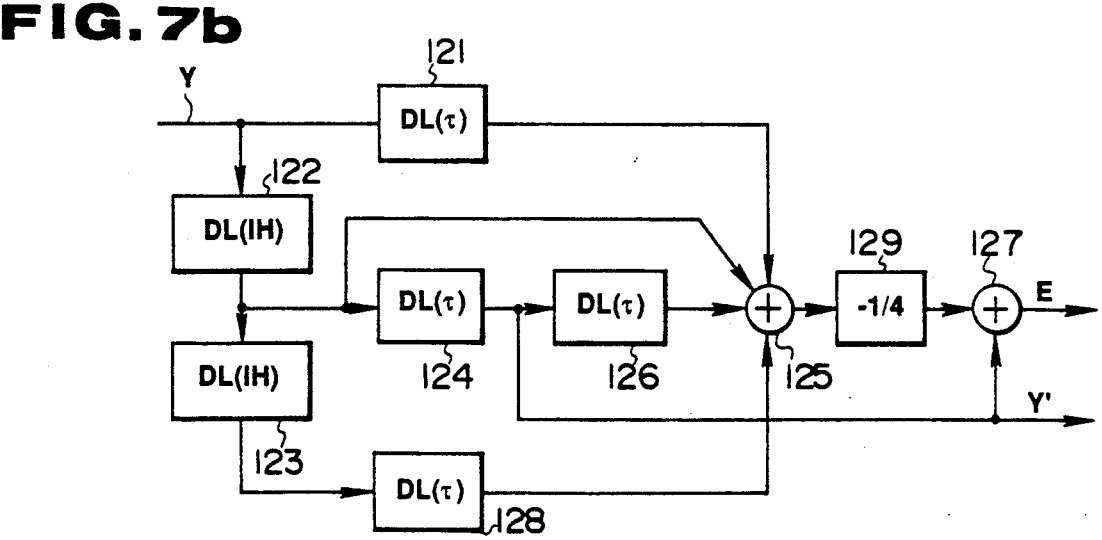

(PRIOR ART)
FIG. 3a
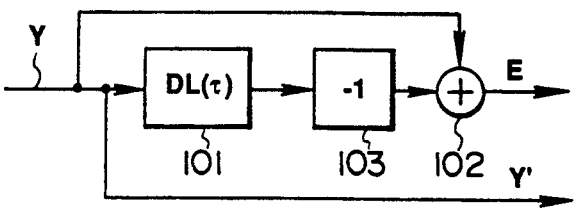
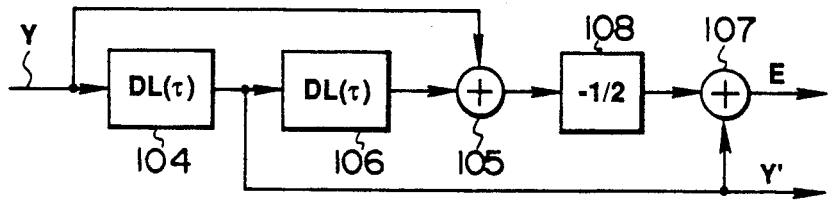
(PRIOR ART)
FIG. 4a
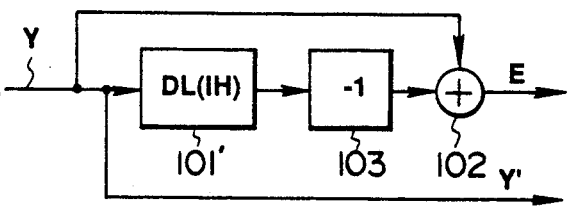
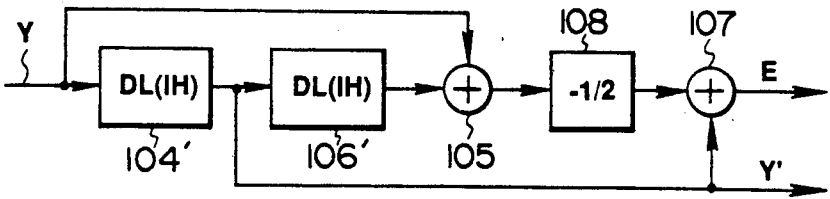

Y'

Y'

OUTPUT OF
SET-UP ADJ. 34

OUTPUT OF
COEFF. 33

OUTPUT OF
COEFF. 35

OUTPUT OF
SET-UP ADJ. 34

OUTPUT Y"
ADDER 36

OUTPUT OF
COEFF. 35

OUTPUT Y"
OF ADDER 36

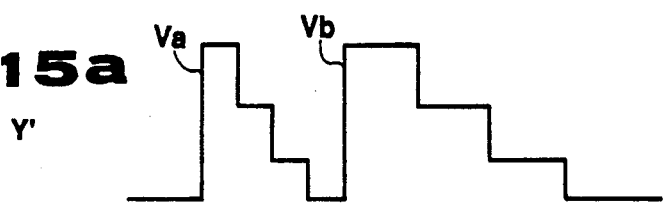
FIG.15a Y'
FIG.15b E
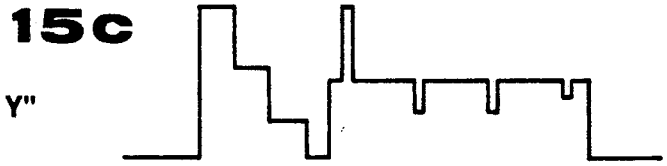
FIG.15c Y''

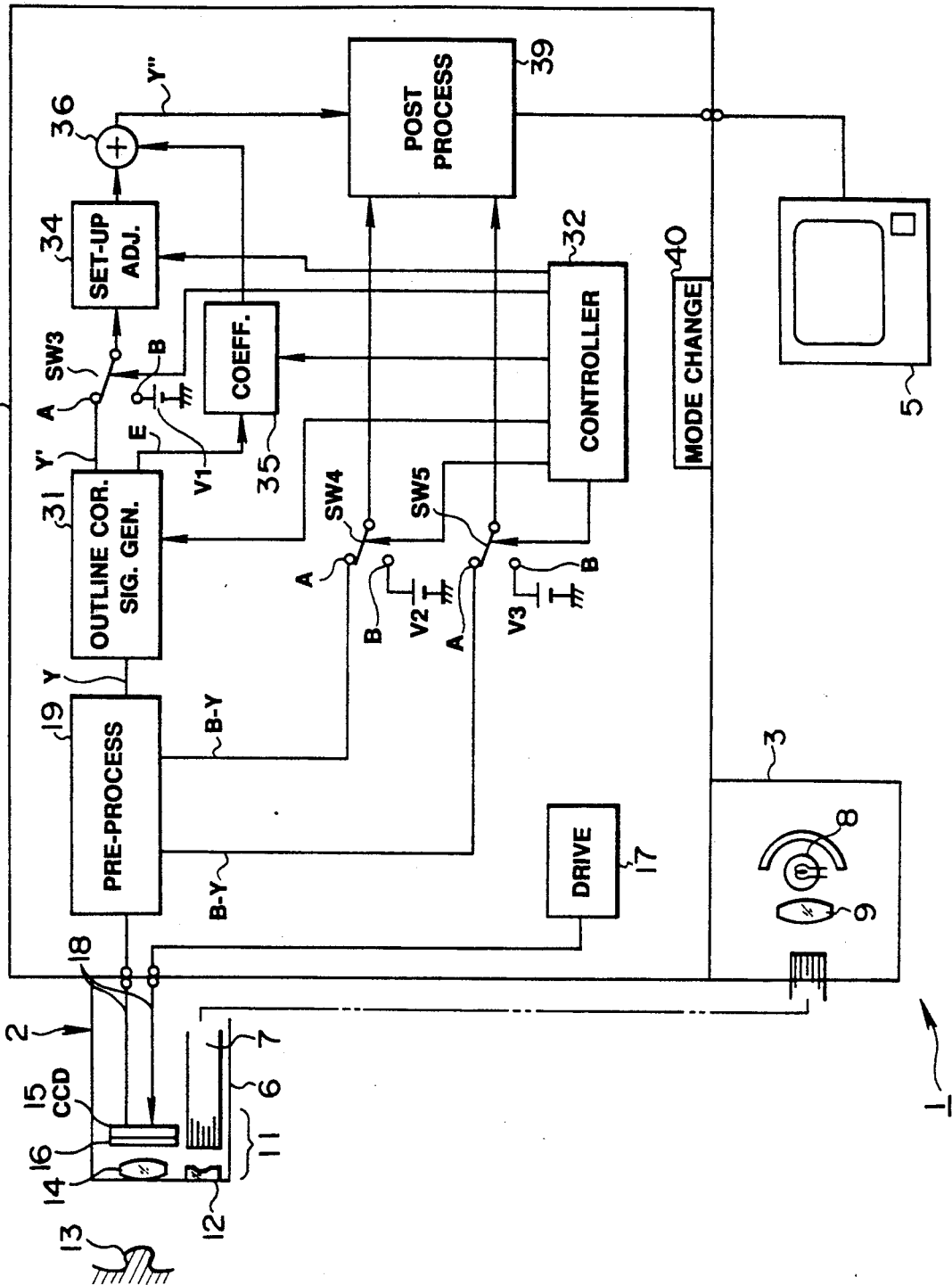

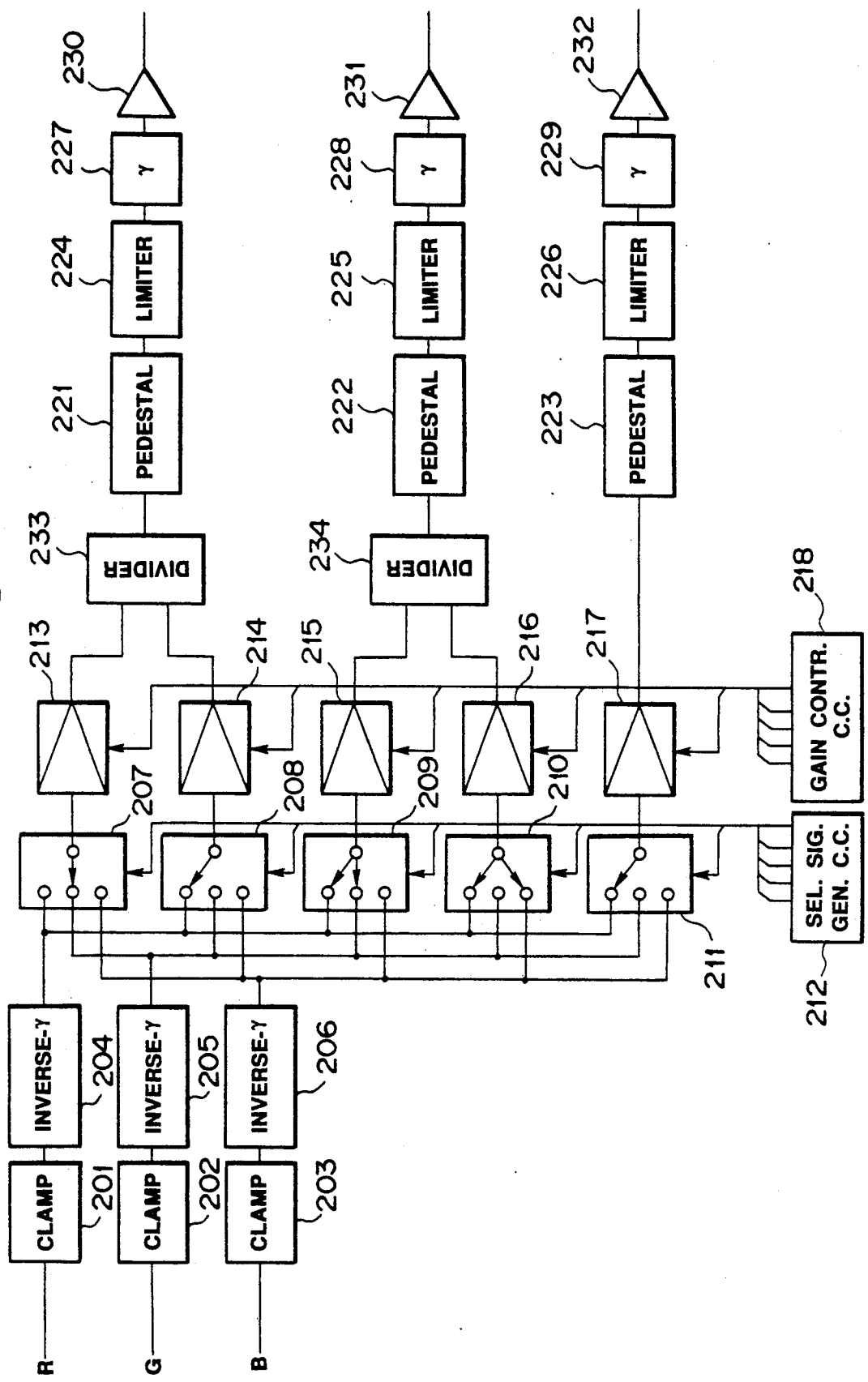

ELECTRONIC ENDOSCOPE APPARATUS SIMULTANEOUSLY DISPLAYING AN ORIGINAL PICTURE IMAGE AND SPECIAL PICTURE IMAGE ON A SINGLE DISPLAYING PICTURE SURFACE

BACKGROUND OF THE INVENTION

Field of the Invention and Related Art Statement

This invention relates to an electronic endoscope apparatus provided with a means of simultaneously displaying an original picture image and special picture image for a video signal.

Recently a medical is extensively used whereby organs within a body cavity can be observed with an elongate insertable part inserted into the body cavity or, as required, various therapeutic treatments are made using treating instruments inserted through a treating instrument channel and an industrial is extensively used whereby the interiors of boilers and engines can be observed with an insertable part inserted into them.

There are also suggested various electronic endoscopes of a system wherein a solid state imaging device as a charge coupled device such (CCD) is provided as an imaging means in the tip part of an insertable part so that picture image information may be taken out as a photoelectrically converted electric signal.

FIG. 1 shows an example of an electronic endoscope apparatus considered to be a related art example.

In FIG. 1, an illuminating light emitted from a light source apparatus (not illustrated) is led to a tip part 83 by a light guide 82 of an electronic endoscope 81 and is radiated to an object 85 through a light distributing lens 84. An image of this object 85, formed by this illuminating light, is formed on a solid state imaging device 87 by an image forming optical system 86. The signal photoelectrically converted by this solid state imaging device 87 is transmitted to a video signal processing circuit 89 through a cable 88, is processed as fixed and is output as video signals as, for example, NTSC and R, G and B signals which are displayed as video images by a color monitor 91 or the like.

The output of the solid state imaging device 87 is input into the video signal processing circuit 89, various noise contained in the solid state imaging device output are reduced in a noise reducing circuit 92, γ is corrected in a γ-correcting circuit and a luminance signal Y and color difference signals R−Y and B−Y are generated by a luminance/color difference separating circuit 94. The luminance signal Y increases the sharpness by an outline correcting circuit 95 and is input together with the color difference signals R−Y and B−Y into an encoder circuit 96 and a video signal is output.

The above mentioned outline correcting circuit 95 is of a formation as is shown in FIG. 2. The output E of the outline correcting signal generating circuit 97 is made G times as large by a coefficient counter 98 as shown in this diagram and is added to a luminance signal Y' in an adder 99. In such a case, the outline correcting amount can be varied by varying the value of the coefficient G of the coefficient counter 98.

The outline correcting system by the above mentioned outline correcting signal generating circuit 97 is largely divided into a horizontal outline correction and vertical outline correction. A horizontal outline correcting signal generating circuit is shown in FIG. 3. A block diagram of a vertical outline correcting signal generating circuit is shown in FIG. 4.

FIGS. 3a and 4a are respectively of a primary outline correcting system wherein a signal equivalent to a primary differential is generated. FIGS. 3b and 4b are respectively of a secondary outline correcting system wherein a signal equivalent to a secondary differential is generated. In FIG. 3a, the luminance signal Y is delayed by about $\tau = 200$ [ns] by a delay line 101, is input into an adder 102 and is directly output as a luminance signal Y'. The output of the above mentioned delay line 101 is output as a signal E with the signal Y added in the above mentioned adder 102 through a coefficient counter 103 making −1 time.

In FIG. 3b, the luminance signal Y is delayed by $\tau$ in the delay line 104 and is input into an adder 105. The output of this delay line 104 is input into a delay line 106 delaying further by $\tau$ and is input into an adder 107 and is also output as a luminance signal Y'.

The output of the above mentioned delay line 106 is added in the adder 105 and the output of this adder 105 is input into the above mentioned adder 107 through a coefficient counter 108 making $-\frac{1}{2}$ time and is output as an outline correcting signal E with the luminance signal Y' added.

FIGS. 4a and b are of the same formation as the formation replaced with delay lines 101', 104' and 106' delaying by 1H (one horizontal scanning period) the delay amounts $\tau$ of the delay lines 101, 104 and 106 in FIGS. 3a and b.

The input signal Y and outputs E and Y' in (FIGS. 3a and b are used as the outline correcting signal generating circuit 97 of the above mentioned FIG. 2 are shown in FIGS. 5 and 6.

A block diagram of an outline correcting signal generating circuit combining these horizontal outline correcting system and vertical outline correcting system is shown in FIGS. 7a and b.

In the outline correcting signal generating circuit shown in FIG. 7a, the luminance signal Y is output directly as a signal Y' and is input into the $\tau$ and 1H delay lines 111 and 112 and the outputs of these delay lines 111 and 112 are added in the adder 113 and then the addition is input into a coefficient counter 114 making $-\frac{1}{2}$ time. The output of this adder 114 is added with the input signal Y in an adder 115 and an output signal E is output.

In FIG. 7b, the input luminance signal Y is input into $\tau$ and 1H delay lines 121 and 122. This signal delayed by 1H is input into a 1H delay line 123 and into a $\tau$ delay line 124 and adder 125. The output of this delay line 124 is further input into a $\tau$ delay line 126 and into an adder 127. The output of the above mentioned delay line 123 is also input into an adder 125 through a $\tau$ delay line 128 and the output of this adder 125 is input into a coefficient counter 129 making $-\frac{1}{4}$ time. The output of this coefficient counter 129 is output as an output signal E through the adder 127. The output of the delay line 124 is output as an output signal Y'.

One of the picture image processes of this video signal is a differentiating process. By making this process, the outline of a picture image can be extracted, the structure and the like of an object can be observed and, for example, for medical use, the structure of an affected part can be observed in detail from the observation of the boundary of the affected part. Particularly, in the above mentioned differentiating process, not only the outline can be extracted but also the manner of the inclination of the rise and fall of the object can be observed.

This process has been heretofore made by an external picture image processing apparatus as a computer by using the output of a video signal processing circuit. As a simple process, there is a suggestion of outputting an outline correcting signal as it is.

However, even if an outline corrected signal or a differential processed picture image is output, it will not be able to be compared with the original picture image and therefore the feature will not be well developed. For example, even if the structure of a part to be noted can be clearly output by enhancing the outline of an original picture image, it will not be able to be simultaneously compared and therefore its advantage will not be able to be well extracted.

For a differentiating process, the picture image will often be very different from the original picture image.

By this differentiating process, some part may be made conspicuous but an unclear part will often be produced.

Thus, with only one picture image, a general diagnosis will be difficult and will be hard to accurately make.

In U.S. Pat. No. 4,712,133, there is disclosed an endoscope apparatus wherein, irrespective of a still picture display, a moving picture is always displayed. However, with the still picture, the information is not very different from that obtained from the moving picture. Therefore, for general diagnosis, information different from that of the moving picture (original picture) is desired to be obtained.

OBJECT AND SUMMARY OF THE INVENTION

An object of the present invention is to provide an electronic endoscope apparatus whereby an endoscope picture image which is used for making a general diagnosis easy can be provided.

Another object of the present invention is to provide an electronic endoscope apparatus which can display an original picture image and a special picture image which can make the outline, structure, tone and the like conspicuous so as to be comparable with each other.

Further another object of the present invention is to provide an electronic endoscope apparatus whereby a special picture image can be obtained in real time.

In the present invention, for an image signal imaged by imaging means, on one hand, an ordinary signal processing is done to display an original picture image/contracted original picture image. On the other hand, a special picture image is processed as a different outline enhancement. A differentiating process and a color enhancing process, from those of the original picture image, are made and both of these picture images are mixed and are displayed on the same displaying picture surface as a standard video signal.

BRIEF DESCRIPTION OF THE DRAWINGS

FIG. 1 is a formation view of an electronic endoscope apparatus considered to be a related art example.

FIG. 2 is a formation view of an outline correcting circuit in FIG. 1.

FIGS. 3a, 3b and 4a, 4b are circuit diagrams of an outline correcting signal generating circuit in FIG. 2.

FIGS. 5a-5c and 6a-6c are waveform views for explaining the operations in FIGS. 3 and 4.

FIG. 7a and 7b are circuit diagrams of another outline correcting signal generating circuit.

FIGS. 8 to 15 relate to the first embodiment of present invention.

FIG. 8 is a general formation view of the first embodiment.

FIG. 9 is a block diagram showing the formation of an outline correcting signal generating circuit.

FIG. 10 is a block diagram showing the formation of a controller.

FIG. 11 is an elevation showing a color monitor displaying a parent and child picture surface.

FIGS. 12, 13a-13d, 14a-14e, 15a-15c are waveform views for explaining the operation of the first embodiment.

FIG. 16 is a formation view of a modification of the first embodiment.

FIG. 28 is a block diagram showing another formation example of the color converting circuit in the sixth embodiment.

DETAILED DESCRIPTION OF THE PREFERRED EMBODIMENTS

Figure 9:
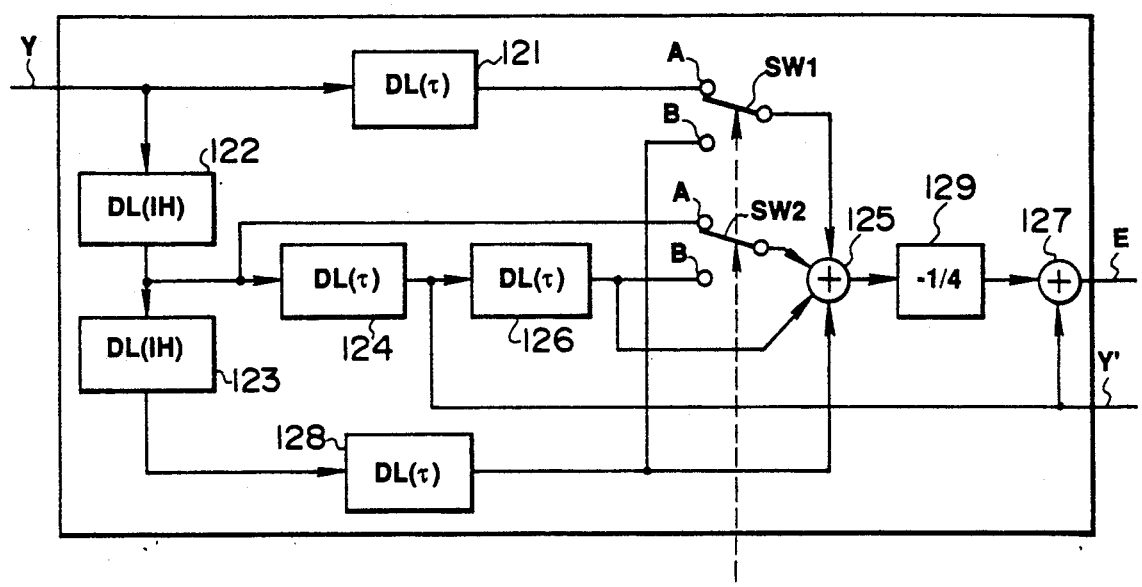

As shown in FIG. 8, an electronic endoscope apparatus 1 of the first embodiment comprises an electronic endoscope (which shall be mentioned also as an electronic scope hereinafter) 2, a light source apparatus 3 feeding an illuminating light to this electronic scope 2, a video signal processing circuit 4 processing the signal for the above mentioned electronic scope 2 and a color monitor 5 color-displaying a videO signal of a predetermined system output from this video signal processing circuit 4.

A light guide 7 to be an illuminating light transmitting means is inserted through an elongate insertable part 6 so that a light guide connector at the rear end (entrance end) of this light guide 7 may be connected to the light source apparatus 3. A white color light of a lamp 8 is condensed and radiated at this entrance end by a condenser lens 9. The illuminating light transmitted by this light guide 7 is further radiated on an object 13 side through a light distributing lens 12 from an exit end fitted to a tip part 11. The object 13 illuminated by the above mentioned illuminating light is made to form an image on a CCD 15 such as a solid state imaging device by an image forming lens 14. A color separating mosaic filter 16 is fitted to the imaging surface of this CCD 15 so as to separate respective pixels into colors, for example, of red, green and blue.

A driving signal output from a driving circuit 17 within the video signal processing circuit 4 is applied to the above mentioned CCD 15 through a signal cable 18. A signal photoelectrically converted by the application of this driving signal and accumulated as an electric charge is read out and is input into a pre-processing circuit 19 which is formed of a color separating circuit 21, an A/D converter 22 A/D converting a luminance signal Y and color difference signals R−Y and B−Y separated in this color separating circuit 21, a first memory 23 and second memory 24 storing the A/D conversion outputs, D/A converters 25 and 26 D/A converting the outputs of these first and second memories 23 and 24 and adders 27 28 and 29 adding respectively both D/A conversion outputs. The above mentioned first memory 23 is a memory to be used for a parent picture surface display and the second memory 24 is a memory to be used for a child picture surface display.

The luminance signal Y output from the above mentioned pre-processing circuit 19 is input into an outline correcting signal generating circuit 31 and a luminance signal Y' and outline correcting signal E are output from this outline correcting signal generating circuit 31.

The block formation of the above mentioned outline correcting signal generating circuit 31 is shown in FIG. 9. This outline correcting signal generating circuit 31 is of a formation wherein changing switches SW1 and SW2 are provided in front of the adder 125 of four inputs in FIG. 7b and the same parts are represented by the same reference numerals. That is to say, it is a simple formation wherein the switches SW$_1$ and SW$_2$, are provided in an existing circuit. These switches SW1 and SW2 are controlled to change by a changing signal of a controller 32. In these switches SW1 and SW2, when the contact A sides are selected to be on as shown in FIG. 9, a secondary outline correcting signal will be generated but, when the contact B sides are selected to be on, a primary outline correcting signal will be generated. When the switch SW1 is in the position A and the switch SW2 is in the position B, the horizontal position will generate a secondary outline correcting signal and the vertical position will generate a primary outline correcting signal. When, in case the switch SW1 is in the position B and the switch SW2 is in the position A, the horizontal position will generate a primary outline correcting signal and the vertical position will generate a secondary outline correcting signal. Thus, in the outline correcting signal generating circuit 31, by changing the switches SW1 and SW2, the primary and secondary outline correcting signals can be generated.

The delayed luminance signal Y' output from the above mentioned outline correcting signal generating circuit 31 is made to be of a size indicated by the controller 32 by a coefficient counter 33, is input into a set-up adjuster 34 and is made to be a set-up value indicated by the controller 32 by this set-up adjuster 34. The outline correcting signal E is made to be the value indicated by the controller 32 by the coefficient counter 35, is added with the luminance signal adjusted in the set-up by an adder 36 as a mixing means and is output as a luminance signal Y''.

The above mentioned luminance signal Y'' is varied to be a signal obtained by outline-correcting, primarily differentiating or secondarily differentiating the pre-process output luminance signal Y by passing the luminance signal Y' and outline correcting signal E through the coefficient counters 33 and 35 controlled by the controller 32, set-up adjuster 34 and adder 36.

By changing the witches SW1 and SW2 in FIG. 9 or adjusting the coefficient counters 33 and 35 or set-up adjuster 34, the output signal of the adder 36 can be obtained as not only an ordinary video signal but also an outline-corrected video signal, primarily or secondarily differentiated output or video signal having such special effect as, for example, applying a large outline correcting signal to a slight luminance signal component.

The color difference signals R−Y and B−Y output through the D/A converter 25 from the first memory 23 are made to be the respective sizes indicated by the controller 32 respectively by the coefficient counters 37 and 38 and are then input into a post-processing circuit 39 together with the luminance signal Y''.

For example, when the adder 36 is a mere differential output, by the controller 32, (the coefficients of the coefficient counters 37 and 38 will be made zero) the color difference signals R−Y and B−Y will be made zero and will be output as black and white picture images or will be able to be output as combined with the increase and decrease of the level of the luminance signal Y' together with the coefficient counter 33. On the signal displayed on the parent picture surface, that is, the signal output from the first memory 23, the above described ordinary picture image and special picture image can be selected but, on the output signal of the second memory 24 displayed on the child picture surface, a contracted picture image of the original picture image made by contracting the ordinary picture image is displayed.

Figure 10:
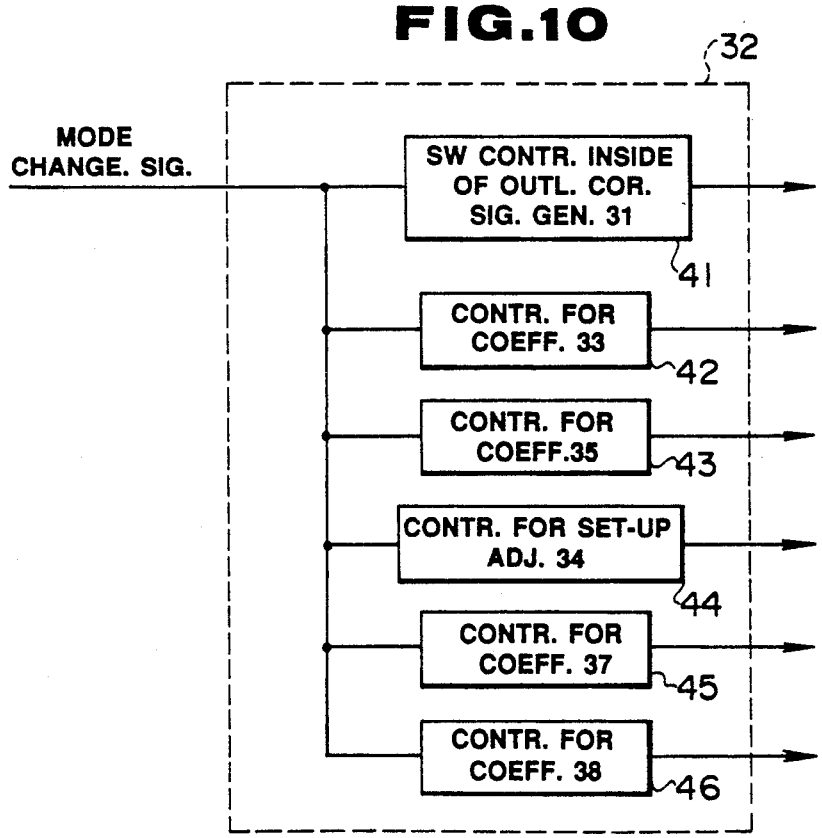

The block formation of the above mentioned controller 32 is shown in FIG. 10. In this controller 32, when a mode changing signal by changing (selecting) a mode changing switch 40 provided, for example, on the operating panel of the video signal processing circuit 4 is received, instructions will be able to be given to the respective controlled objects in response to this mode changing signal.

Figure 11:
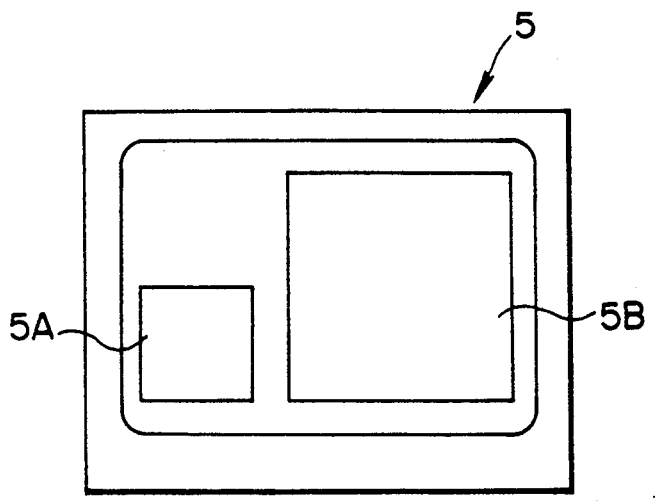
Figure 12:
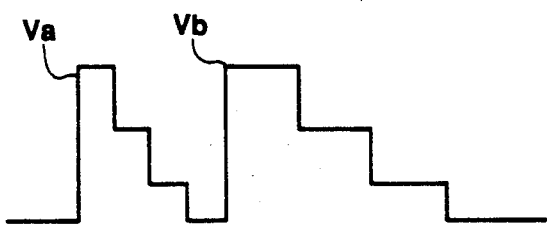

The mode changing signal is formed from an outline correcting signal generating circuit interior switch controlling part 41, coefficient counter 33 controlling part 42, set-up adjuster controlling part 44, coefficient counter 37 controlling part 45 and coefficient counter 38 controlling part 46. These respective controlling parts are to be changed at the time of the child picture surface output and parent picture surface output. Therefore, the parent picture surface and child picture surface can display respectively differently processed picture images. For example, on the displaying picture surface of the color monitor 5, as shown in FIG. 11, a child picture surface 5A and parent picture surface 5B are displayed adjacently in the horizontal direction. By the memory controller 20, the second memory 24 is read out prior to the first memory 23 and, in one horizontal period signal, as shown in FIG. 12, a child picture surface displaying signal Va read out of the second memory 24 and a parent picture surface displaying signal Vb read out of the first memory 23 are separated from each in the horizontal direction and are output from the pre-processing circuit 19.

In this case, the signal Va will be contracted to be, for example, the signal Vb divided by an integer. The signals Va and Vb output from the pre-processing circuit 19 can be displayed in different picture image processing states by changing the coefficient state of the coefficient counter or the like. In this first embodiment, the child picture surface (displaying) signal Va is set in an ordinary moving picture display. On the other hand, the parent picture surface (displaying) signal Vb is displayed as variously processed in the picture image.

The above mentioned (outline correcting circuit interiior) switch controlling part 41 controls the change of the switches SW1 and SW2 within the outline correcting circuit 31. Also, by the coefficient counter 33, 35, 37 and 38 controlling parts 42, 43, 45 and 46 and set-up adjuster controlling part 44, instructing voltages or instructing data are transmitted to these respective control objects to control the coefficient values of the respective coefficient counters 33, 35, 37 and 38 and the set-up value of the set-up adjuster 44.

The luminance signal Y″ and color difference signals R−Y and B−Y input into the above mentioned post-processing circuit 39 are matrix-processed, encoder-processed, superimposing-processed and mask-processed, are output as video signals of a predetermined system and are color-displayed by the color monitor 5.

The operation of this first embodiment shall be explained in the following with reference to FIG. 13.

First of all, the picture image process of the parent picture surface signal Vb shall be described.

The signal Y′ made by delaying through the outline correcting signal generating circuit 31 the luminance signal Y output from the pre-processing circuit 19 and the outline correcting signal E are output.

Figure 13A:
Figure 13B:
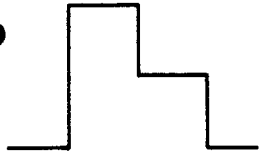
Figure 13D:
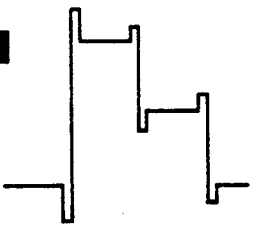

For example, if the luminance signal Y′ in one horizontal scanning period is a signal of the waveform shown, for example, in FIG. 13a and the outline correcting mode is selected by the mode changing means 40, the coefficient of the coefficient counter 33 will be set to be 1 by the controller 32, the set-up value of the set-up adjuster 34 will be made zero (that is, the input signal will be output as it is) and the output of this set-up adjuster 34 will be the same signal as the luminance signal Y′ as shown in FIG. 13b. On the other hand, if the above mentioned outline correcting signal E is made a secondary outline correcting signal, the output of the coefficient counter 35 will be a signal of the waveform shown in FIG. 13c. This signal is added with the output (FIG. 13b) of the above mentioned set-up adjuster 34 by the adder 36 to be a luminance signal Y″ corrected in the outline of the picture image as shown in FIG. 13d.

Figure 14A:
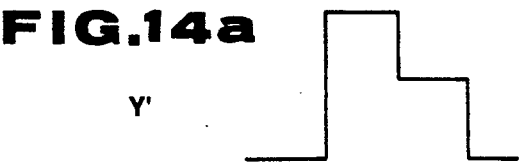
Figure 14B:
Figure 13C:
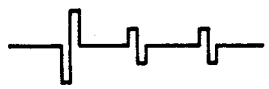
Figure 14C:
Figure 14D:
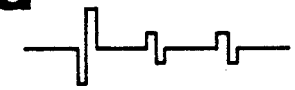
Figure 14E:
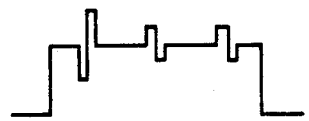

If the secondary differential picture image mode is selected, the controller 32 will set the coefficient of the coefficient counter 33 to be zero for the luminance signal Y′ shown in the above mentioned FIG. 13a or 14a and the output of this coefficient counter 33 will be as shown in FIG. 14b, will be set at some set-up value as shown in FIG. 14c by the set-up adjuster 34 and will be added with the outline correcting signal output of the coefficient counter 35 shown in FIG. 14d by the adder 36 to be a signal Y″ as is shown in FIG. 14e. This will be a secondary differential output of the input luminance signal Y′. In this case, it will be a secondary differential output. However, if the outline correcting signal generating circuit 31 is made a primary outline correcting signal generating mode, the output of the adder 36 will be a primary differential output.

The luminance signal Y″ of these outline correcting mode, secondary differential mode and primary differential mode can be obtained.

The color difference signals R−Y and B−Y are controlled in setting the coefficients of the coefficient counters 37 and 38 by the controller 32 in response to the mode in which the above mentioned luminance signal Y′ is processed.

For example, when the adder 36 is a mere differential output, a black and white picture image will be able to be output by making the coefficients of the coefficient counters 37 and 38 zero and the color difference signals R−Y and B−Y will be also able to be increased or decreased in response to the increase or decrease of the luminance signal Y′ in conformity with the coefficient of the coefficient counter 33.

As shown in FIG. 12, when the above mentioned child picture surface signal Va and parent picture surface signal Vb are output, when the ordinary picture image mode is selected in the mode changing switch 40, ordinary moving pictures will be displayed on both picture surfaces 5A and 5B. When the special picture image (differential picture image) is selected for the parent picture surface 5B, the signals Va and Vb shown in FIG. 15 will be output from the pre-processing circuit 19 and will be input into the next step side. In this case, the controller 32 will control the outline correcting signal generating circuit 31, respective coefficient counters 33, 35 and 38 and set-up adjuster 34 so that an ordinary picture image may be output in the timing of the child picture surface 5A and signals as are shown respectively in FIGS. 15a, b and c may be output in Y′, E and Y″ in FIG. 8. That is to say, an original picture made by contracting an ordinary picture image will be displayed in the timing of the child picture surface.

On the other hand, in the timing of the parent picture surface, the above mentioned controller 32 controls the respective coefficient counters 33, 35, 37 and 38, outline correcting signal generating circuit 31 and set-up adjuster 34 so that Y′, E and Y″ in FIG. 8 may be the signals shown in FIGS. 15a, b and c. That is, in the parent picture surface 5B, the special picture image (differential picture image) can be displayed. In FIG. 15, an example of a primary differential picture image is shown as the special picture image.

According to this first embodiment, with a comparatively simple formation combined with an existing outline correcting circuit and by a real time process, an original picture image can be displayed on the child picture surface and a special picture image processed by the outline correction, primary differential and secondary differential can be displayed on the parent picture surface.

As an original picture image and special picture image are simultaneously displayed on the same displaying picture surface, for example, when a picture image of a manner different from that of the original picture image is obtained by a special picture image process, to what parts of the original picture image the respective parts of the picture image correspond will be able to be easily known.

Therefore, for example, by variously changing the picture image on the special picture image processing side, any part hard to distinguish in the original picture image can be made conspicuous to be used as diagnosis judging material.

Thus, an auxiliary means effective to generally diagnosing a part to be noted is made.

There can be formed a modification wherein the coefficient counters 23, 27 and 28 in the above mentioned first embodiment are formed of switches SW3, SW4 and SW5 and direct current sources V1, V2 and V3 as in a video signal processing circuit 4' shown in FIG. 16.

In the modification shown in FIG. 16, control signals for changing the outline correcting signal generating circuit 31 and respective switches SW3, SW4 and SW5 and instructing voltages or instructing data to the coefficient counter 35 and set-up adjuster 34 are transmitted by the controller 32.

In the case of this modification shown in FIG. 16, when the contacts A are selected in the switches SW3, SW4 and SW5, an ordinary video signal output will be made, but when the contacts B are selected to be switched, if any set-up value is held by the set-up adjuster 24, the video output will be of a black and white differential picture image.

In the above mentioned first embodiment or modification, the child picture surface 5A is not limited to be an ordinary picture image (original picture image) as contracted but may be of an outline enhanced to an ordinary degree.

Also, the setting of the respective coefficient counters 33, 35, 37 and 38 and outline correcting signal generating circuit 31 in the child picture surface 5A may be varied to be of a value adapted to the display in response to the contraction rate of the child picture surface.

In the case of this modification, the luminance signal is switched to a direct current level by the SW3 and is thereby set up but may be switched by the SW3 not to the direct current level but to a signal having a set-up, that is, to a signal on a square wave.

For the first embodiment, the color difference signal is increased or decreased by the coefficient counter or changed to a direct current level by a switch but, by having a level set-up value between the coefficient counter or switch and post-process, the differential picture image can be colored with any color.

In FIG. 1, in the pre-process circuit 19, the picture images of the parent picture surface and child picture surface, that is, the first memory output picture image signal and second memory output picture image signal are once D/A converted to be analogue signals and are added but the respective picture image signals may be added as digital signals as they are and may be then D/A converted and made a pre-process circuit output signal.

Figure 17:
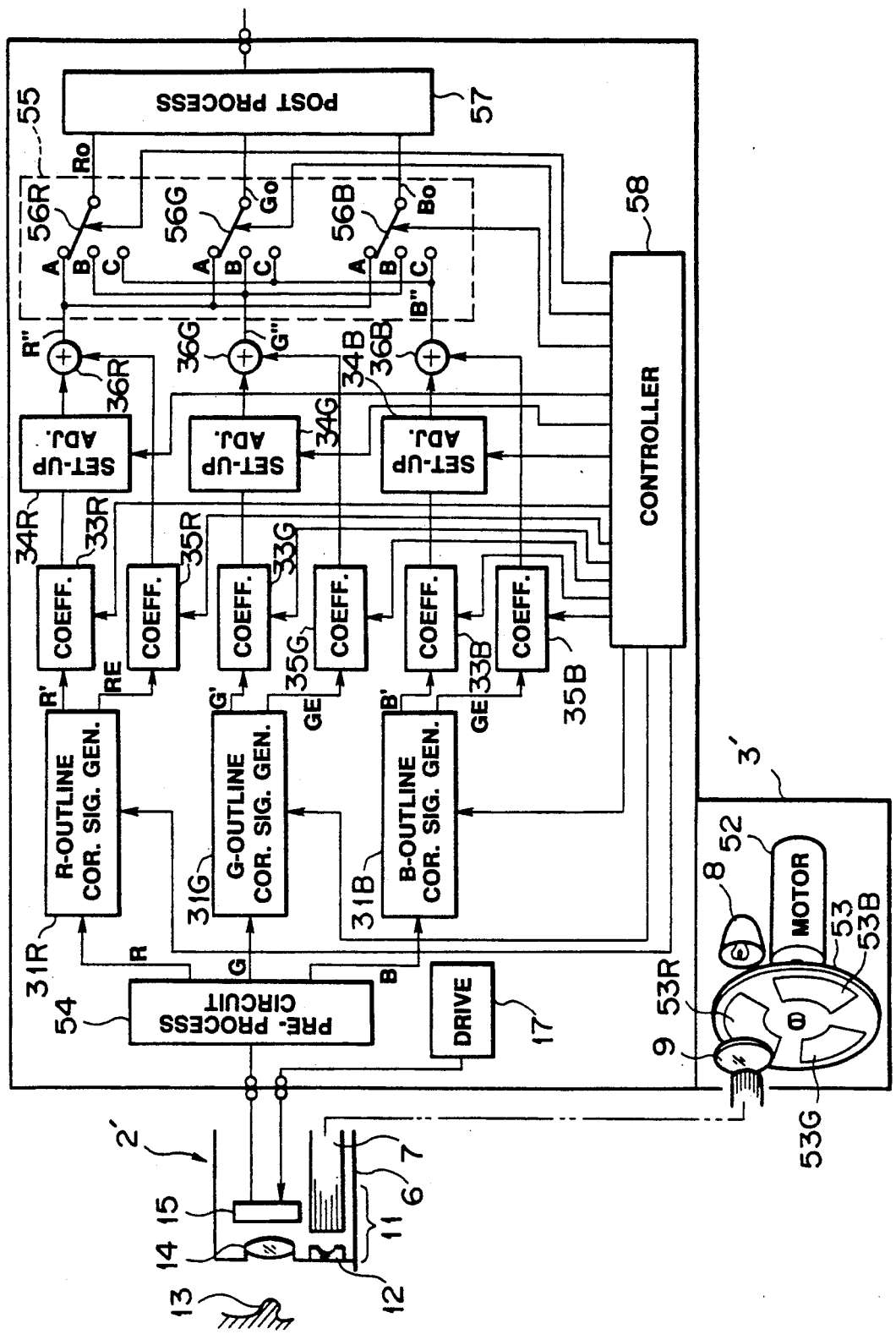
FIG. 17 is a formation view of the second embodiment of the present invention.

FIG. 17 shows the second embodiment of the present invention.

In this embodiment, an electronic scope 2', for example, of a frame sequential system is used and a light source apparatus 3' outputting color light of red, green and blue is used.

The above mentioned electronic scope 2' has no color separating mosaic filter 16 in the electronic scope 2 shown in FIG. 8.

The light source apparatus 3' has a rotary filter 53 rotated by a motor 52 arranged between the lamp 8 and condenser lens 9 in the light source apparatus shown in FIG. 8. In this rotary filter 53, three sector-like apertures are provided in a light intercepting disc and red, green and blue color transmitting filters 53R, 53G and 53B are fitted to the apertures so that, when these filters 53R, 53G and 53B are sequentially interposed in an illuminating light path, a white color light will be made red, green and blue color light.

A CCD 15 of the above mentioned electronic scope 2' is read out by the application of a driving signal of a driving circuit 17 and is input into a pre-process circuit 54 and R, G and B color signals are output.

The above mentioned R, G and B color signals are input respectively into an R outline correcting signal generating circuit 31R, G outline correcting signal generating circuit 31G and B outline correcting signal generating circuit 31B. The color signals I' (I'=R', G' and B') of the respective outline correcting signal generating circuits 31I (I=R, G and B) are input into set-up adjusters 34I through coefficient counters 33I and the outline correcting signals IE (IE=RE, GE and BE) are added with the output signals of the above mentioned set-up adjusters 34I by adders 36I through coefficient counters 35I.

The signals I'' (I''=R'', G'' and B'') added by the above mentioned adder 36I are input into a post-process circuit 57 through switches 56I forming an output selecting circuit 55.

The above mentioned R, G and B outline correcting signal generating circuits 31R, 31G and 31B, coefficient counters 33R, 33G, 33B, 35R, 35G and 35B, set-up adjusters 34R, 34G and 34B and switches 56R, 56G and 56B are controlled by a controller 58.

The above mentioned outline correcting signal generating circuits 31R, 31G and 31B are of the same formation as of one another and are of the same formation as of the outline enhancing signal generating circuit 31 shown in FIG. 9.

Therefore, the color signals R', G' and B' output from these outline enhancing signal generating circuits 31R, 31G and 31B correspond to the signal Y' in FIG. 8 and the R, G and B outline correcting signals RE, GE and BE correspond to the outline correcting signal E. Therefore, in this embodiment, too, the signals RE, GE and BE can be selected as primary and secondary outline correcting signals by changing the switches.

For example, the signal R' output from the R outline correcting signal generating circuit 31R passes through the coefficient counter 33R and set-up adjuster 34R, is added by the adder 36R with the outline correcting signal RE having become a predetermined size through the coefficient counter 35R and is output as an output signal R''. In the same manner, the signals G' and B' also pass respectively through the coefficient counters 33G and 33B and set-up adjusters 34G and 34B and are added respectively by the adders 36G and 36B with the outline correcting signals GE and BE having passed respectively through the coefficient counters 35G and 35B to be output signals G'' and B''.

These signals R'', G'' and B'' correspond to the signal Y'' in the first embodiment.

For example, when the coefficient of the coefficient counters 33R, 33G and 33B is made 1 and is made equal to that of the input signals R', G' and B' and the set-up amount in the set-up adjusters 34R, 34G and 34B is set to be zero, the signals RE, GE and BE passed through the coefficient counters 35R, 35G and 35B respectively made to be of the same coefficient and the signals R'', G'' and B'' added by the adders 36R, 36G and 36B will be video signals outline-corrected by the amount set by the coefficient counters 35R, 35G and 35B in the same manner as in the first embodiment.

When the signals R', G' and B' are made zero by the coefficient counters 33R, 33G and 33B, are made to be respectively of the same set-up values by the set-up adjusters 34R, 34G and 34B and are added by the adders 36R, 36G and 36B with the signals RE, GE and BE having passed through the coefficient counters 35R, 35G and 35B, the output signals R", G" and B" will become differential signals of the R, G and B signals having respectively the same set-up values.

The output signals R", G" and B" of these adders 36R, 36G and 36B are input into switches 56R, 56G and 56B forming the output selecting circuit 55. These switches 56R, 56G and 56B are controlled in switching by the controller 32 so that signals Ro, Go and Bo may be output through contacts J (J=A, B and C) respectively selected by this switching control.

These signals Ro, Go and Bo are input into a post-process circuit 57, are processed by a matrix, masking and superimposing and are output as video signals of a predetermined system.

For example, in case the signals R", G" and B" output from the adders 36R, 36G and 36B are ordinary outline-corrected video signals as in the above, when the switch 56R of the output selecting circuit 55 selects the contact A, the switch 56G selects the contact B and the switch 56B selects the contact C, the video output will be an ordinary outline-corrected video signal. In this case, if the contact A is selected respectively by the switches 56R, 56G and 56B, the video output will be a black and white video image of outline-corrected R. In the same manner, if the contact B or C is selected by the switches 56R, 56G and 56B, a black and white video image of the outline-corrected G or B signal will be made.

In case the signals R", G" and B" are differential outputs of the R, G and B signals as in the above, if the contact A is selected by the switch 56R of the output selected circuit 55, the contact B is selected by the switch 56G and the contact C is selected by the switch 56B, the video output will be a differential signal colored with a severe variation of a video signal on a grey back.

In this case, if the contact A is selected by the switches 56R, 56G and 56B, a differential picture image of the R signal will be obtained. In the same manner, if the contact A is selected by the switches 56R, 56G and 56B or the contact B is selected by these switches 56R, 56G and 56B, the differential outputs of the respective R, G and B signals will be obtained and the manner of the variation of the respective color components will be able to be observed.

Further, various special effects are obtained by varying the conditions of the respective coefficient counters, set-up adjusters and switches in the same manner as in the first embodiment. Also, the differential picture image can be colored by making the levels of the set-up adjusters 34R, 34G and 34B different. On the child picture surface, the same as in the first embodiment, the respective coefficient counters and others are set so that an ordinary picture image may be displayed and, for the signal of the parent picture surface, as described above, various processed special picture images can be displayed.

In the above mentioned second embodiment, the pre-process circuit 54 has, for example, R, G and B frame memories, the signal data imaged under R, G and B illuminating light are stored once in the r, G and B frame memories by one frame and the video signal data stored by one frame in these frame memories are simultaneously read out to output synchronized R, G and B signals. In this case, if dual port memories are used for the R, G and B frame memories, the writing in and reading out will be able to be made in parallel and real time video signals processed as described above will be able to be produced for the R, G and B signals output from this pre-process circuit 54.

The above mentioned second embodiment is for the electronic scope 2' provided with a color imaging means of a frame sequential system but can be applied also to the case of the electronic scope 2 provided with the mosaic filter 16 of the first embodiment. In this case, the pre-process circuit 19 may be used in place of the pre-process circuit 54 and further the luminance signal Y and color difference signals R−Y and B−Y may be converted to R, G and B signals through a matrix circuit.

The picture image process of the first embodiment can be applied also to the electronic scope 2' of the frame sequential system. In this case, too, the R, G and B signals may be converted to Y, R−Y and B−Y signals through a matrix circuit.

It is apparent that this picture image process can be applied also to the output signal of the imaging means fitting a TV camera having a mosaic filter built-in or a frame sequential type TV camera to the eyepiece part of such an optical endoscope as not only the electronic scopes 2 and 2' but also the fiber scope. (see FIG. 27).

In case a memory means for stilling a picture image is located within the pre-process circuit 19 or 54 or post-process circuit 39 or 57, for example, in case a differential picture image is output, the still picture image will be able to be also observed. Particularly, in case the picture image stilling means is within the pre-process circuit, the original picture image and differential picture image of the still picture image will be able to be freely selected and displayed. This still differential picture image may be displayed in a monitor or the like or may be photographed or the video signal may be stored directly in a picture image file or the like so as to be able to be promptly utilized for the diagnosis or the like of an affected part. The child picture image is not limited to be contracted but also may be displayed at the same magnification as of the parent picture surface. In such a case, if the displaying area is short, the peripheral side may be cut in displaying. (It shall be explained in the embodiment shown in FIG. 19).

Figure 18:
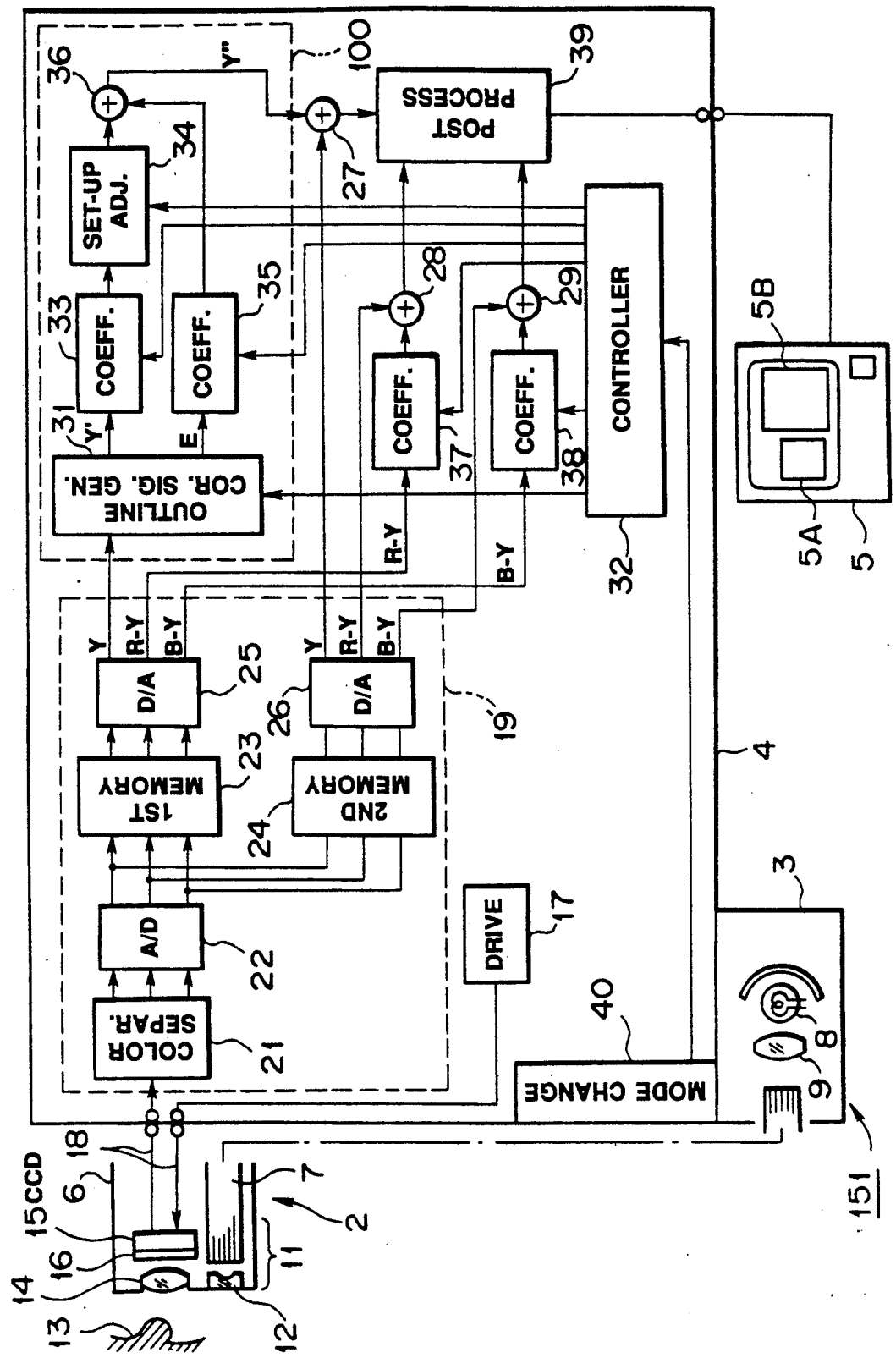
FIG. 18 is a formation view of the third embodiment of the present invention.

FIG. 18 shows an electronic endoscope apparatus 151 of the third embodiment of the present invention.

The same components as in the first embodiment are represented by the same reference numerals.

In the first embodiment, the parent picture surface displaying signal and child picture surface displaying signal are added (mixed) before the circuit of processing the picture images for the parent picture surface displaying signal, whereas, in this third embodiment, the parent picture surface displaying signal and child picture surface displaying signal are added (mixed) in the step after the picture image processing circuit for the parent picture surface displaying signal.

That is to say, in this embodiment, the adders 27, 28 and 29 are provided respectively in the steps before the post-process circuit 39 and the parent picture surface displaying luminance signal Y" having passed through the setup adjusting circuit 34, the parent picture surface displaying color difference signals $(R-Y)''$ and (B−Y)" having passed respectively through the coefficient counters 37 and 38 and the child picture surface displaying luminance signal Y and color difference signals R−Y and B−Y having passed through the D/A converter 26 are respectively added and are input into the post-process circuit 39.

In this embodiment, the pre-process circuit 19' separately outputs the parent picture surface (displaying) signal Vb and child picture surface (displaying) signal Va.

The parent picture surface signal Vb is processed in the picture image the same as in the first embodiment and is then added with the child picture surface signal Va not processed in the picture image.

First of all, the picture image processing on the parent picture surface signal Vb shall be described.

The signal Y' obtained by delaying the luminance signal Y output from the pre-process circuit 19' through the outline correcting signal generating circuit 31 and the outline correcting signal E are output.

If the luminance signal Y', for example, in one horizontal scanning period is a signal of a waveform shown, for example, in FIG. 13a and an outline correcting mode is selected, then the coefficient of the coefficient counter 33 will be set to be 1 by the controller 32, the set-up value of the set-up adjuster 34 will be made zero (that is to say, the input signal will be output as it is) and the output of this set-up adjuster 34 will be the same signal as the luminance signal Y' as shown in FIG. 13b. On the other hand, if the above mentioned outline correcting signal E is made a secondary outline correcting signal, the output of the coefficient counter 35 will be a signal of the waveform shown in FIG. 13c and this signal will be added with the output (FIG. 13b) of the above mentioned set-up adjuster 34 by the adder 36 to be a luminance signal Y" corrected in the outline of the picture image as shown in FIG. 13d.

Then, for example, if a secondary differential increasing mode is selected, the controller 32 will set the coefficient of the coefficient counter 33 to be zero for the luminance signal Y' shown in the above mentioned FIG. 13a or 14a and the output of this coefficient counter 33 will be as shown in FIG. 14b. The output will be set at some set-up value as shown in FIG. 14c by the set-up adjuster 34 and will be added with the outline correcting signal output of the counter 35 shown in FIG. 14d by the adder 6 to be such signal Y" as is shown in FIG. 14e. This will be a secondary differential output of the input luminance signal Y'. In this case, it will be a secondary differential output. However, if the outline correcting signal generating circuit 31 is made a primary outline correcting signal generating mode, the output of the adder 36 will be a primary differential output.

The luminance signals Y" of these outline correcting mode, secondary differential mode and primary differential mode can be obtained.

On the other hand, the color difference signals R−Y and B−Y are controlled in the coefficient setting of the coefficient counters 37 and 38 by the controller 32 in response to the mode in which the above mentioned luminance signal Y' is processed.

For example, in case the adder 36 is of a mere differential output, if the coefficients of the coefficient counters 37 and 38 are made zero to be able to output a black and white picture image, the color difference signals R−Y and B−Y will be able to be also increased or decreased in response to the increase or decrease of the luminance signal Y' in conformity with the coefficient of the coefficient counter 33.

In this embodiment, in case the child picture surface signal Va is output from the second memory 24, in this child picture surface signal Va, the luminance signal component will be composited with the luminance signal Y" processed in the picture image by the adder 27 to be of the same waveform as in FIG. 12c. Also, the color difference signals R−Y and B−Y of the child picture surface signal are composited with the output signals of the coefficient counters 37 and 38 respectively by the adders 38 and 29.

These composited luminance signal and color difference signals are processed as predetermined by the post-process circuit 39 and are output.

In the first embodiment, it is necessary to change the timings of the parent picture surface and child picture surface in the picture image processing part but, in this third embodiment, it is not necessary to change the timings and, even if the picture image is processed on the entire picture surface, the same results as in the first embodiment will be able to be obtained.

Figure 19:
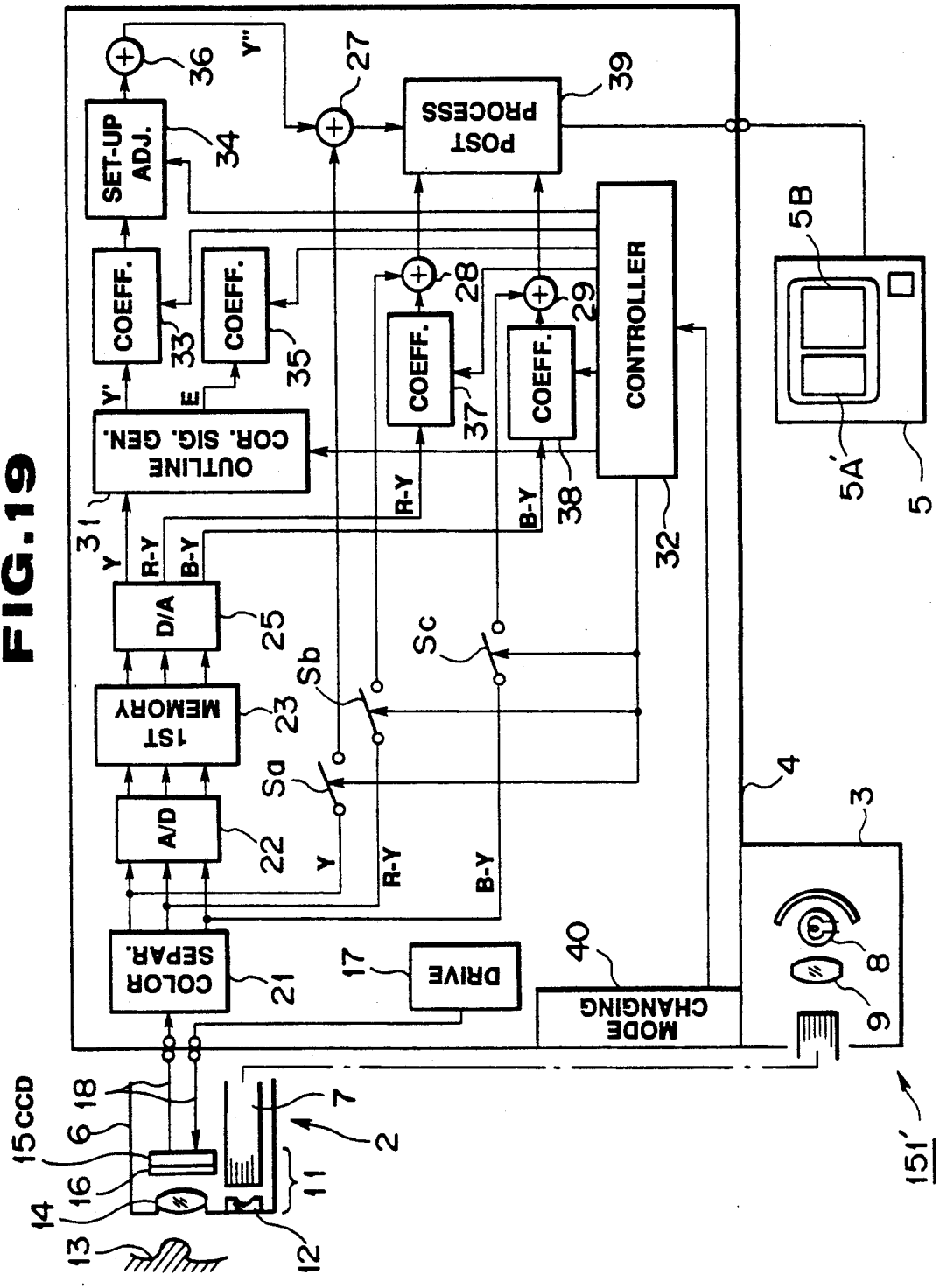
FIG. 19 is a formation view of a modification of the third embodiment.

FIG. 19 shows an apparatus 151' of a modification of the third embodiment. In this modification, the second memory 24 and D/A converter 26 for displaying the child picture surface are omitted.

In FIG. 18, the output signal of the color separating circuit 21 is input into the A/D converter 22 and is also input into the adders 27, 28 and 29 respectively through the switches Sa, Sb and Sc.

The above mentioned switches 27, 28 and 29 are controlled to be on/off for example, by the controller 32 and are to be on only in the horizontal period in which the parent surface is not overlapped. Therefore, in this case, the picture image 5A' in which the displayed size in the horizontal direction of the ordinary picture image is partly narrowed (that is to say, cut on the peripheral side) is made in the color monitor 5 as shown in FIG. 19 and is displayed adjacently to the parent picture surface 5B.

Figure 20:
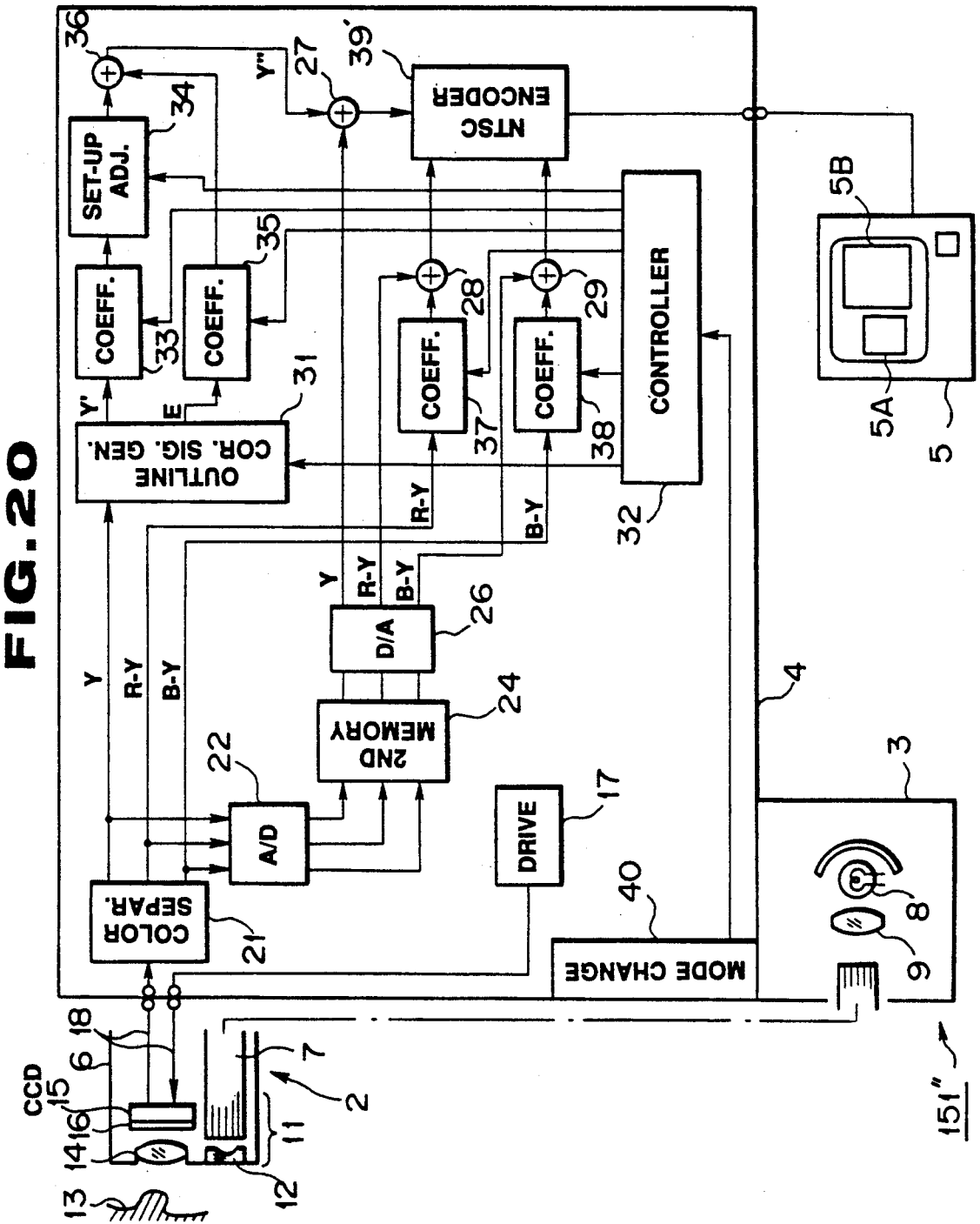
FIG. 20 is a formation view of another modification of the third embodiment.

In FIG. 19, the memory 24 on the child picture surface side is not provided but, as shown in FIG. 20, an apparatus in which the memory 22 on the parent picture surface side is omitted may be made.

In this case, the same as in the case of FIG. 18, the child picture surface 5A and parent picture surface 5B will be displayed adjacently to each other in the color monitor 5.

In this modification, the output signals of the adders 27, 28 and 29 are made an NTSC composite video signal by an NTSC encoder 39' to be output to the color monitor 5.

Figure 21:
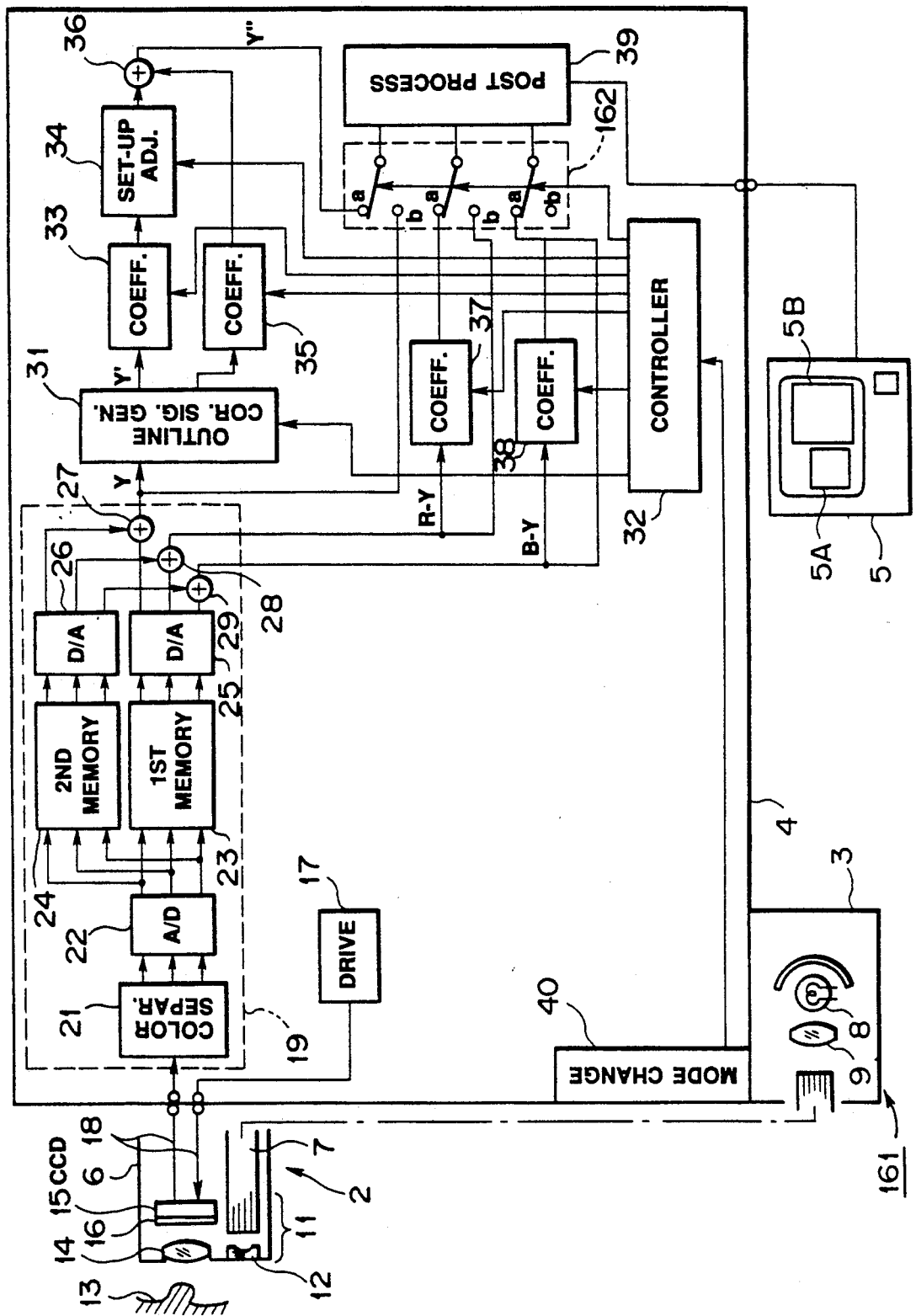
FIG. 21 is a formation view of the fourth embodiment of the present invention.

FIG. 21 shows an electronic endoscope apparatus 161 of the fourth embodiment of the present invention.

In this embodiment, the luminance signal Y output from the adder 27 is input into the outline correcting signal generating circuit 31 and is input also into (the contact b of) the picture image changing circuit 162 in the first embodiment shown in FIG. 8.

The color difference signals R−Y and B−Y output from the adders 28 and 29 are input respectively into the coefficient counters 37 and 38 and into the picture image changing circuit 162.

The signal input into the above mentioned outline correcting signal generating circuit 31 is processed in the picture image over the entire picture surface the same as in the third embodiment and is input into the picture image changing circuit 162 together with the output signals of the coefficient counters 37 and 38 through the adder 36.

That is to say, both child picture surface and parent picture surface are processed in the picture images to be special picture images. In the same manner, the color difference signals input into the coefficient counters 37 and 38 are processed as explained in the third embodiment. Both child picture surface and parent picture surface are set at gains adapted to special picture images. Therefore, the luminance signal and color difference signals processed in the picture images on both child picture surface and parent picture surface are input into the input terminal a of the picture image changing circuit 162.

On the other hand, the original signals of the child picture surface and parent picture surface are input into the input terminal b of the picture image changing circuit 162.

In the picture image changing circuit 162, the switch is changed so that the input terminal b may be selected at the timing when the child picture surface signal is input and the input terminal a may be selected at the timing when the parent picture surface signal is input and, on the post process circuit 39 side, the child picture surface becomes an original picture image and the parent picture surface becomes a special picture image to obtain the same waveform as is shown in FIG. 12c.

The picture surfaces are processed as determined in this post-process circuit 39 and are displayed in the color monitor 5.

Figure 22:
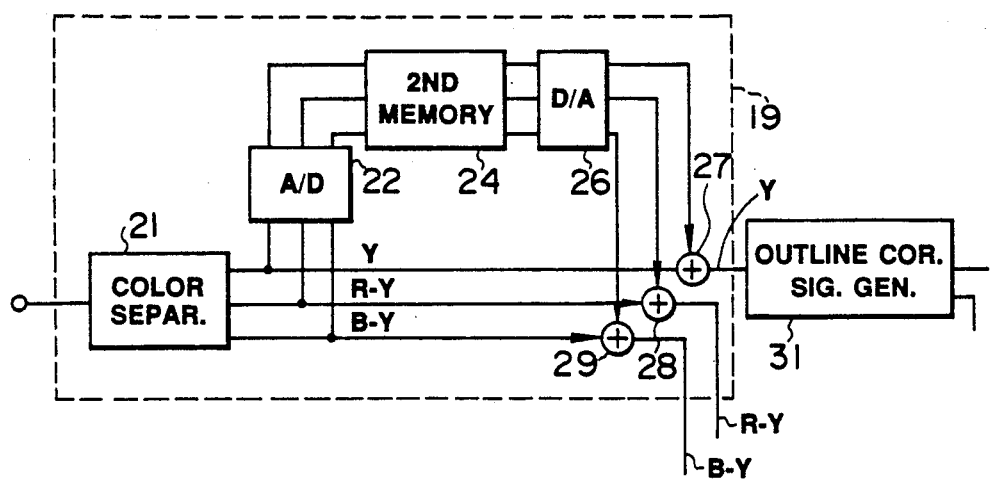
FIG. 22 is a formation view of an essential part of a modification of the fourth embodiment.

FIG. 22 shows the formation of an essential part of a modification of the fourth embodiment of the present invention.

In this modification, the first memory 23 and D/A converter 25 are omitted in FIG. 21 and the signal of the parent picture surface is read out at such timing as is displayed on the right side in FIG. 11.

It is apparent that, in the first to fourth embodiments, the means of compositing the respective signals of the child picture surface and parent picture surface is not limited to the adders 27, 28 and 29 but may be any thing that is changed by a switch.

Figure 23:
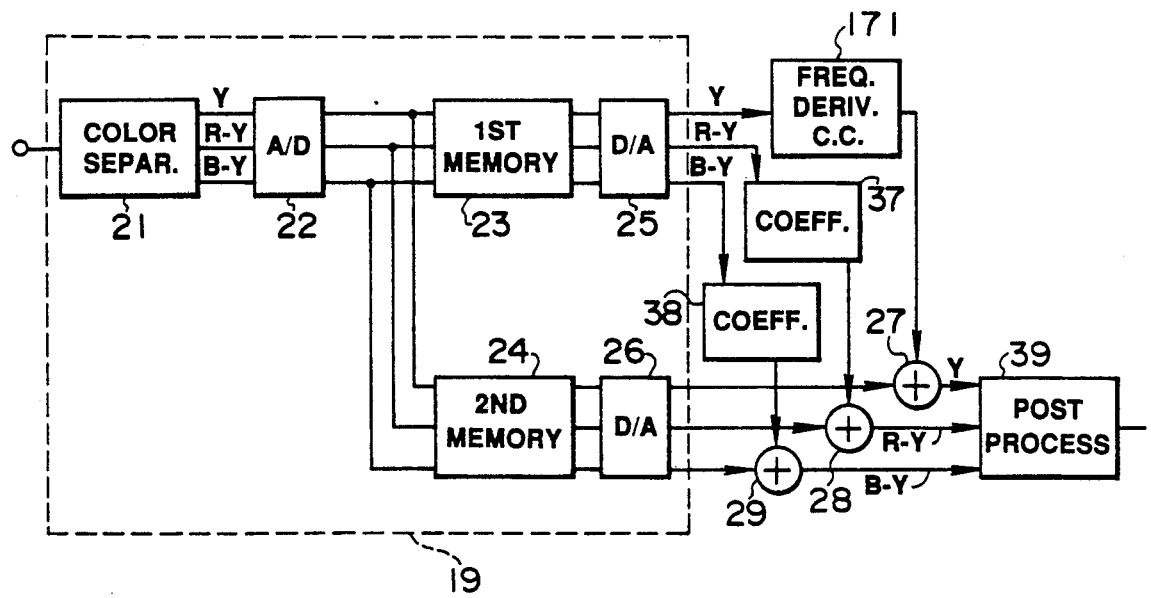
FIG. 23 is a formation view of an essential part of the fifth embodiment.

FIG. 23 shows an essential part of the fifth embodiment of the present invention. In this embodiment, in FIG. 18, the child picture surface signals output from the A/D converter 26 of the pre-process circuit 19 are output respectively to the adders 27, 28 and 29, the luminance signal Y corresponding to the parent picture surface and output from the D/A converter 25 is input into the frequency extracting circuit 171 and the color difference signals R−Y and B−Y are input respectively into the coefficient counters 37 and 38.

The output of the above mentioned frequency extracting circuit 171 is input into the adder 27 and is composited with the child picture surface luminance signal.

Figure 24:
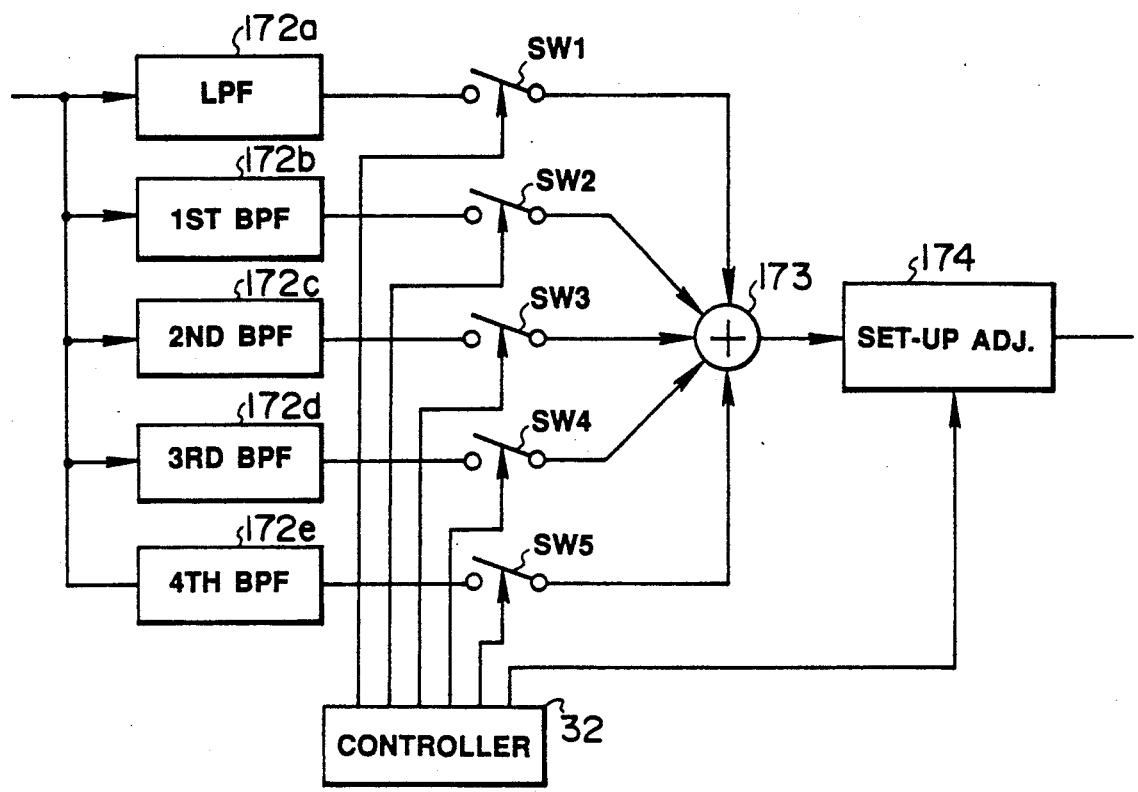
FIG. 24 is a block diagram showing the formation of a frequency extracting circuit in the fifth embodiment.

The above mentioned frequency extracting circuit 171 is a circuit extracting and outputting a specific frequency component contained in the luminance signal Y. An example of this circuit 171 is shown in FIG. 24.

The input luminance signal Y is added by the adder 173 through the switches SW1 to SW5 in series with the low pass filter 172a, first to fourth band pass filters 172a to 172e and respective filters 172i (i=a to e).

The output of this adder 173 is input into the adder 27 through the set-up adjusting circuit 174 and is composited with the luminance signal of the child picture surface.

Figure 25:
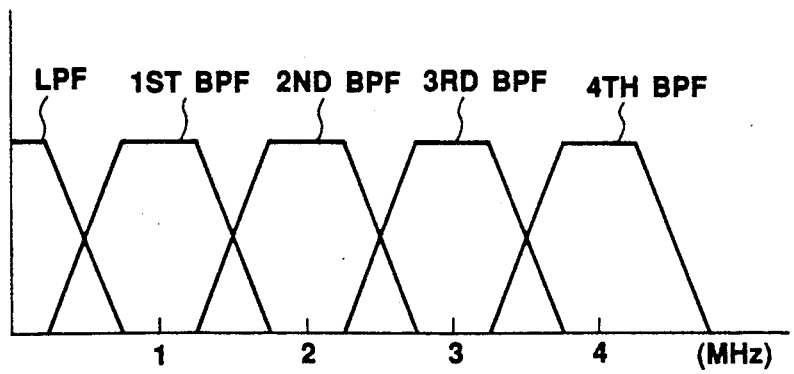
FIG. 25 is a characteristic diagram showing transmittive characteristics of respective filters.

The color difference signals are the same as are shown in FIG. 18. The above mentioned switches SW1 to SW5 are controlled to be on/off by the controller 32. Also, the set-up adjusting circuit 174 is controlled in the set-up value by the controller 32. The passed frequency characteristics of the above mentioned respective filters 172a to 172e are shown in FIG. 25.

When all the switches SW1 to SW5 are closed, all the bands to the vicinity of 4 MH$_z$ will be passed.

When the switches SW1, SW2 and SW5 are opened but the switches SW3 and SW4 are closed, the component near 2 to 3 MH$_z$ of the input signal will be extracted. In this case, as the low frequency component of the input signal (luminance signal) will be interrupted, the output is made by applying a proper set-up with the set-up adjusting circuit 174.

The others are of the same formation as in the above mentioned third embodiment. According to this fifth embodiment, the luminance component can be enhanced for any desired frequency band.

In this embodiment, coefficient counters may be formed instead of the switches SW1 to SW5 and the amplitude of the signal for the respective frequency components may be freely varied.

In this fifth embodiment, for example, in the third embodiment, the parts of the numerals 31, 33 to 36 (represented by the numeral 100) are replaced with a frequency extracting circuit 171. It is apparent that, in other embodiments, too, the parts of these numerals 31, 33 to 36 can be replaced with the frequency extracting circuit 171 in the same manner.

Figure 26:
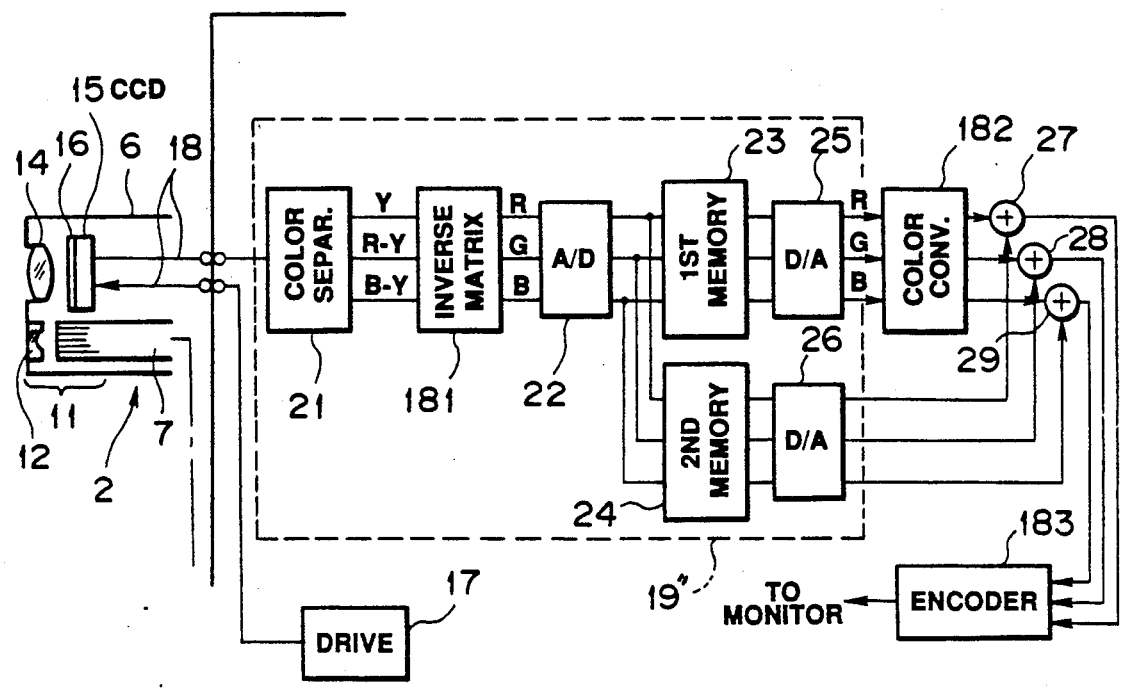
FIG. 26 is a formation view of an essential part of the sixth embodiment of the present invention.

An essential part of the sixth embodiment of the present invention is shown in FIG. 26.

In this embodiment, in the third embodiment shown in FIG. 18, the output of the color separating circuit 21 is converted by the inverse matrix circuit 181 to R, G and B signals which are converted to digital signals by the A/D converter 22 and are input respectively into the first memory 23 and second memory 24. The output signal of the first memory 23 is returned by the D/A converter 25 to analogue color signals R, G and B which are input into a color converting circuit 182. The output signals of this color converting circuit 182 are input respectively into the adders 27, 28 and 29, are composited with the color signals obtained by converting the output signals of the second memory 24 by the D/A converter 26 and are output to an encoder 183. The output signal of this encoder 183 is displayed in the color monitor 5.

Figure 27:
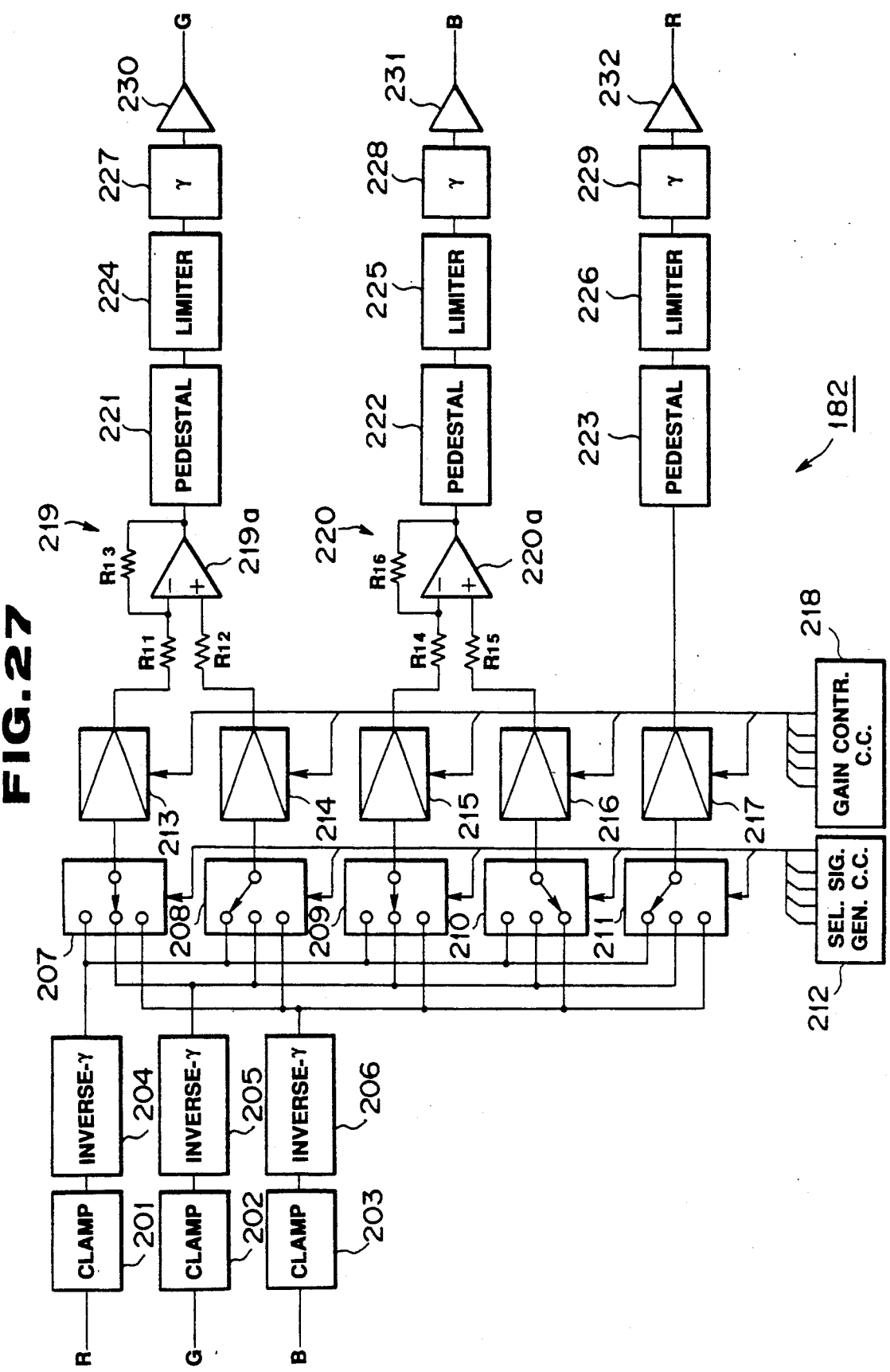
FIG. 27 is a block diagram showing the formation of a color converting circuit in the sixth embodiment.

The pre-process circuit of this embodiment is represented by the reference numeral 19''. The formation of the above mentioned color converting circuit 182 is shown in FIG. 27. The input signals R, G and B are clamped by clamping circuits 201 to 203 and are input into inverse γ-circuits 204 to 206. The signals γ-corrected in the electronic endoscope apparatus are inversely γ-corrected and are corrected so that the video signal level and video image brightness may be in a linear relation.

In the respective circuits 207 to 211, one of the respective signals of R, G and B is selected in response to the signal generated by the selected signal generating circuit 212. Here, as examples, a G signal well showing the distribution of hemoglobin on a mucous membrane and an R signal having little variation are selected respectively in selector circuits 207 and 208, the gains of variable gain amplifiers 213 and 214 are designated in the control circuit 218, the G and R signals are amplified by these gains by the above mentioned variable gain amplifiers 213 and 214 and the above mentioned G and R signals are multiplied by a predetermined coefficient.

The G signal and B signal high in the correlation between the picture images on a general mucous membrane are selected by selector circuits 209 and 210 and are multiplied by a predetermined coefficient by variable gain amplifiers 215 and 216.

The outputs of the above mentioned variable gain amplifiers 213 and 214 are input into a differential amplifying circuit 219 and the level difference between those video signals is calculated. Also, in a differential amplifier circuit 220, the level difference between the video signals which are the outputs of the variable gain amplifiers 215 and 216 is calculated. In the two video signals obtained by thus calculating the level difference, the average value of the signal levels is made substantially equal to the average value of the video signals at the displaying time so that the above mentioned level difference may be displayed to be maximum. The video signals having the pedestals adjusted in pedestal setting circuits 221 and 222 are limited to be within the displayable signal level ranges by limiter circuits 224 and 225, are γ-corrected by γ-correcting circuits 227 and 228 so as to be displayed in a television monitor and are output respectively as video image signals of G and B through buffer circuits 230 and 231.

On the other hand, in the selector circuit 211, an R signal forming the tone of the entire mucous membrane surface is selected and is input into the variable gain amplifier 217. In this variable gain amplifier 217, in order to set the gain so as to give no sense of difference to the tone at the displaying time with the final television monitor, the pedestal level is adjusted by a pedestal level setting circuit 223 and the output of this variable gain amplifier 217 is limited to be within the displayable signal level range by a limiter circuit 226, is γ-corrected by a γ-correcting circuit 229 so as to be displayed in the television monitor and is output as a video signal of R through a buffer circuit 232.

According to this embodiment, as the difference between the G signal and R signal can be displayed, a red generating part of a delicate tone difference can be detected and, as the difference between the G signal and B signal high in the correlation can be enhanced and displayed, a slight affected part can be detected and thereby there is an effect that the diagnosablity will improve.

Also, the boundary or the like of a slight dyeing at the time of dyeing with methylene blue or the like can be enhanced in real time.

In this embodiment, with a logarithmic amplifier provided in the variable gain amplifier, picture image data proportional to the respective color concentrations can be obtained. The color converting circuit 182 is not limited to the one shown in FIG. 28 but may be the one shown in FIG. 27.

The color converting circuit 182 shown in FIG. 28 is provided with division circuits 232 and 234 instead of the differential amplifying circuits 219 and 220 in the circuit 182 in FIG. 27. The other formations are the same as are shown in FIG. 27.

The circuit in FIG. 28 is of the same operation as of the circuit in FIG. 27. A video signal selected by the selector circuit 207 is amplified by the amplifying rate designated by the gain control circuit 218 and is output from the variable gain amplifier 213. In the same manner, the video signal selected by the selector circuit 298 is amplified by the same or different amplifying rate as or from that of the above mentioned variable gain amplifier 213 and is output by the gain control circuit 218 from the variable gain amplifier 214.

The video signals output from the above mentioned variable gain amplifiers 213 and 214 are input into a division circuit 233 and the ratio of both video signals is calculated.

In the same manner, the respective video signals selected by the selector circuits 209 and 210 are amplified by the variable gain amplifiers 215 and 216 and are input into a division circuit 234 in which the ratio of both video signals is calculated.

The video signals output from the above mentioned division circuits 233 and 234 have the pedestal levels set by the pedestal level setting circuits 221 and 222, are limited by the limiter circuits 224 and 225 to be only the signals within the displayable range or effective data range as video signals, are γ-corrected by the γ-correcting circuits 227 and 228 so as to be displayed in the television monitor and are output through the buffer circuits 230 and 231.

In FIG. 28, there is not only the same effect as of the circuit of FIG. 27, as the influence of the brightness between the respective video signals by the distance can be canceled and therefore the color variation on the mucous membrane surface can be enhanced without being influenced by the shadow by calculating the ratio between the two video signals, but also there is an effect of improving the diagnosability.

Even in this sixth embodiment, the first or second memory 23 or 24 can be omitted as in FIGS. 19, 20 and 21.

Figure 29:
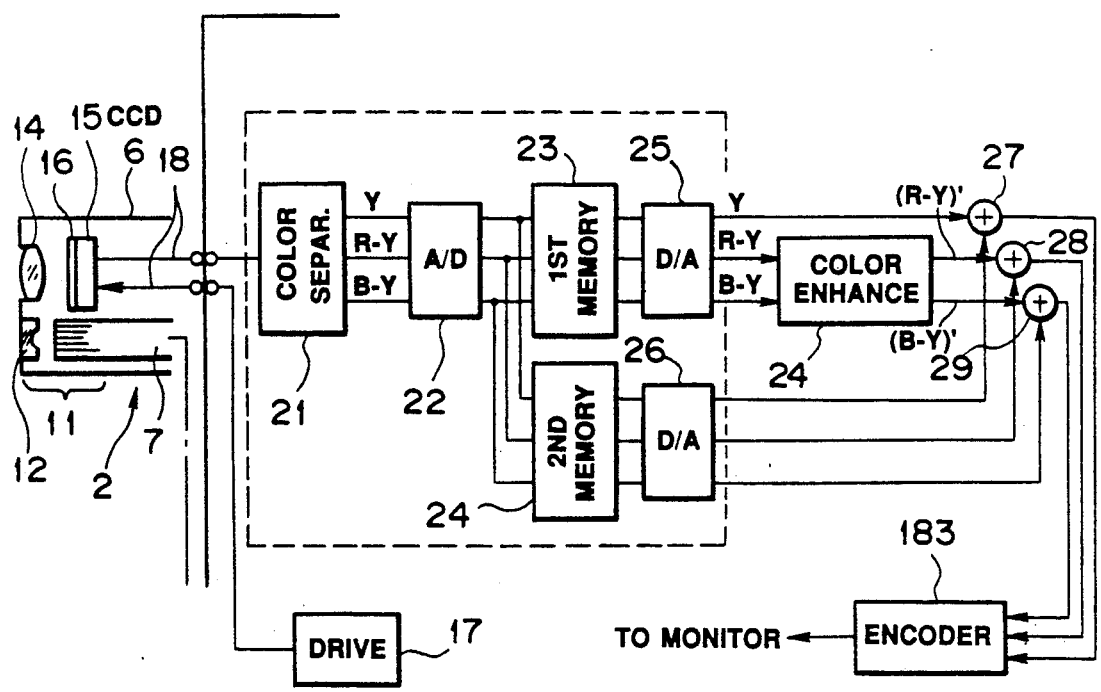

FIG. 29 shows an essential part of the seventh embodiment of the present invention. In this embodiment, in the formation shown in FIG. 26, the inverse matrix circuit 181 is not used. That is to say, the luminance signal Y and color difference signals R−Y and B−Y of the color separating circuit 21 are input into the first memory 23 and second memory 24 through the A/D converter 22.

The output signal of the first memory 23 is converted to an analogue signal through the D/A converter 25, the luminance signal Y is composited with the luminance signal coming through the D/A converter 26 of the second memory 24 by the adder 27 and the color difference signal R−Y and B−Y are made color-enhanced color difference signals (R−Y)' and (B−Y)' by the color enhancing circuit 241 and are then added respectively with the child picture surface color difference signals by the adders 28 and 29.

The output signals of the above mentioned adders 27, 28 and 29 are converted to a composite video signal by the encoder 183 to be output to a color monitor.

Figure 30:
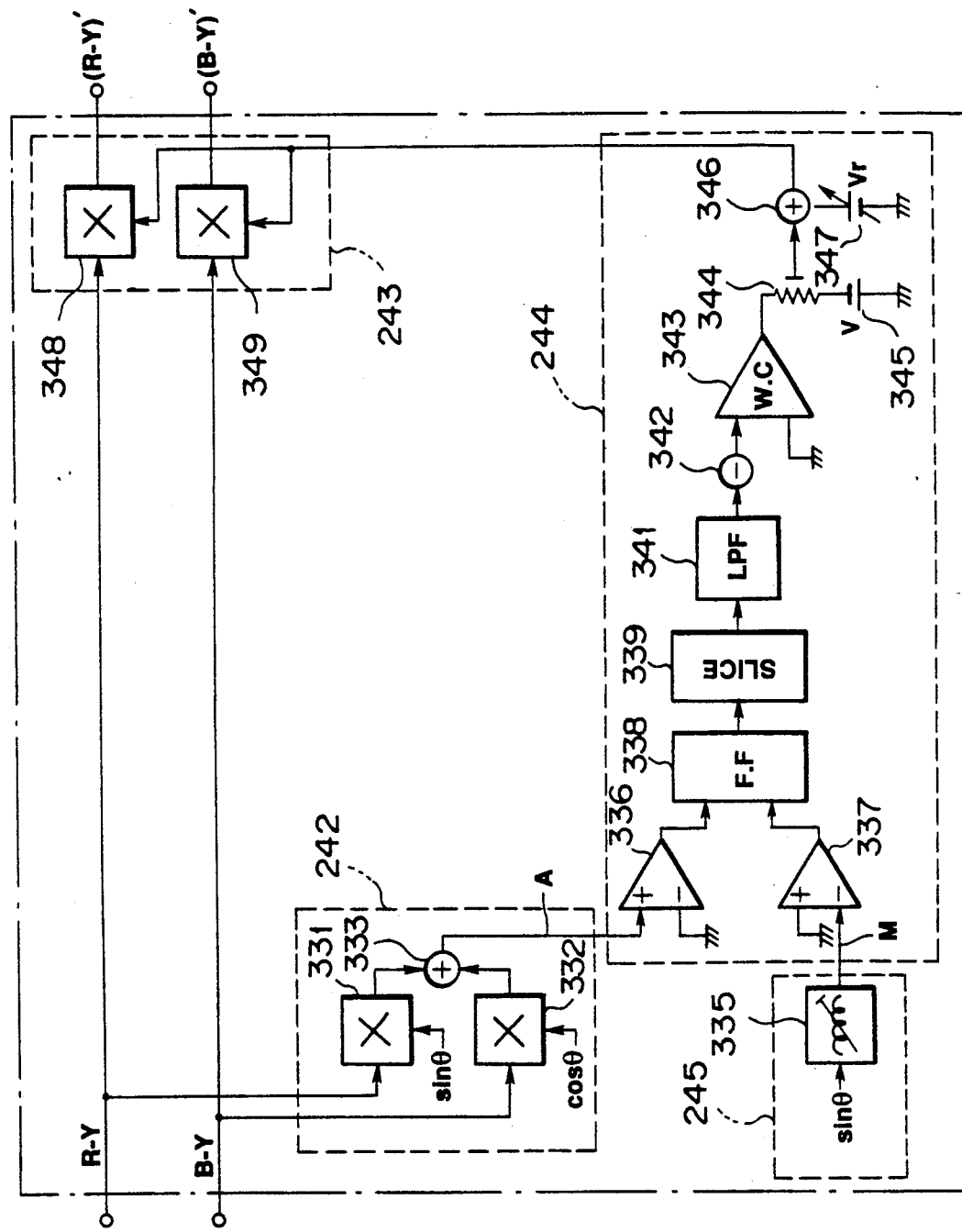
FIG. 30 is a formation view of a color enhancing circuit in the seventh embodiment.

The disclosure of the Japanese patent application laid open No.313989/1988 shown in FIG. 30 can be used for the formation of the above mentioned color enhancing circuit 241.

The color difference signals R−Y and B−Y are input into a rectangularly intersecting modulating circuit 242 with sine waves and cosine waves and into a chroma enhancing circuit 243 enhancing the chroma.

The output of the above mentioned rectangularly intersecting modulating circuit 242 is input into a hue difference enhancing circuit 244, the hue difference of the coloredness designated by an enhanced color designating circuit 245 is output to the above mentioned chroma enhancing circuit 243, the chroma is enhanced for the hue component desired to be enhanced and the color difference signals $(R-Y)'$ and $(B-Y)'$ are output from the output ends.

Figure 31:
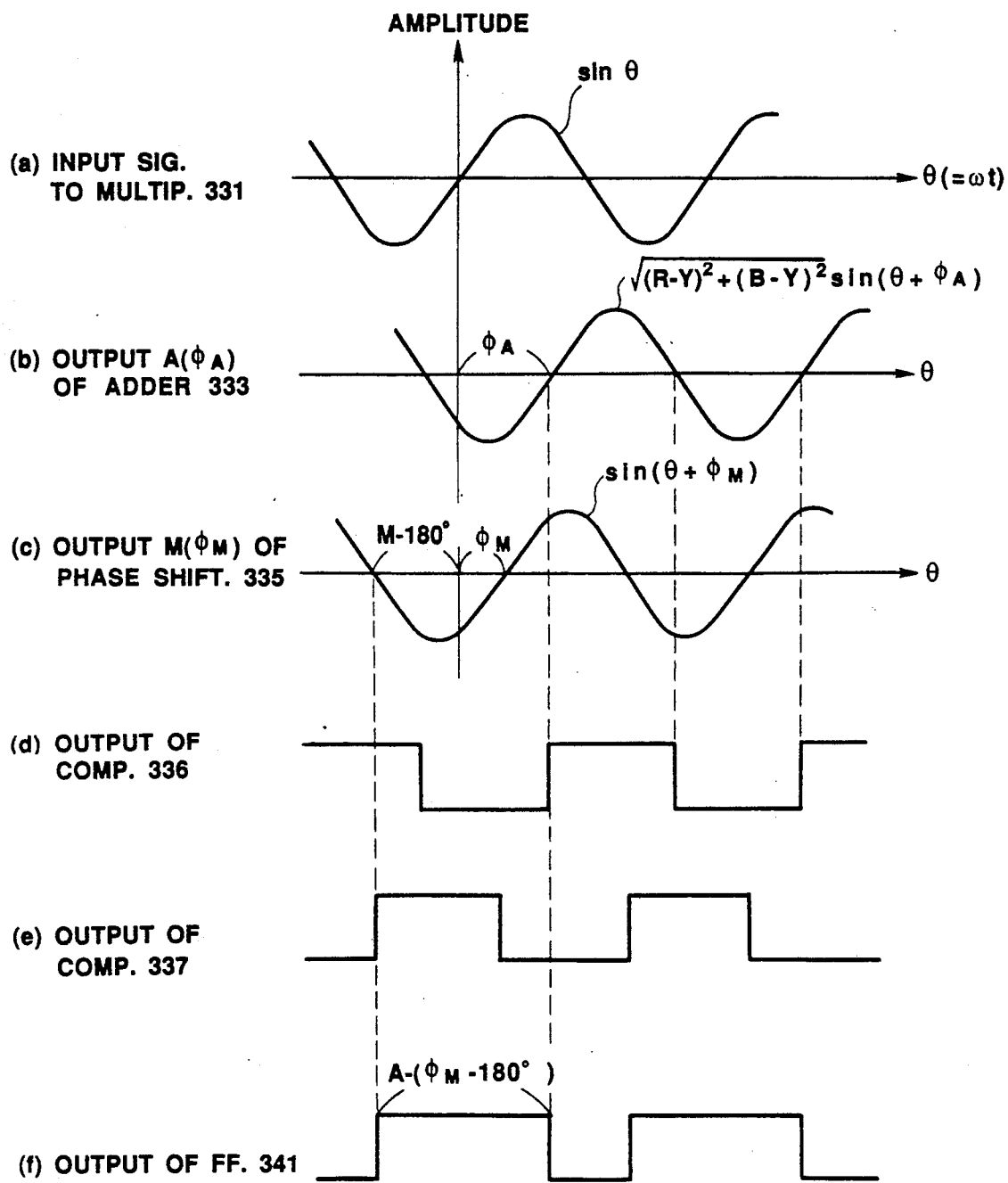
FIG. 31 is an operation explaining view of a color enhancing circuit.

The color difference signals $R-Y$ and $B-Y$ input into the above mentioned rectangularly intersecting modulating circuit 242 are multiplied by signals of $\sin\theta$ and $\cos\theta$ respectively by multipliers 331 and 332, are then added by the adder 333 and are output as a rectangular phase modulated signal A $(\phi_A)$. In this case, if the signal of 3.58 MHz used in the NTSC encoder is used for $\sin\theta$ and $\cos\theta$, the existing circuit will be able to be favorably used and the output signal A $(\phi_A)$ will be $$\sqrt{(R-Y)^2 + (B-Y^2)} \; \sin(\theta + \theta_A)$$

as shown in FIG. 31b for the $\sin\theta$ shown in FIG. 31a. This phase angle is $\phi_A = \tan^{-1}(R-Y)/(B-Y)$.

On the other hand, the above mentioned enhanced color designating circuit 245 consists of a phase shifter 335 and outputs a hue signal M $(\phi_M)$ which is to be enhanced. This output waveform is shown in FIG. 31c.

The output signal A of the above mentioned rectangularly intersecting modulating circuit 242 and the output signal M of the phase shifter 335 are input respectively into comparators 336 and 337 forming the hue difference detecting circuit 244 and a signal compared with 0 potential is output. The above mentioned output signal A is applied to the non-inverted input end of the comparator 336 and outputs a signal of such waveform as is shown in FIG. 31d and the output signal M of the phase shifter 335 is applied to the inverted input end and a waveform shown in FIG. 31c is output. The inverted output is utilized for this comparator 336 to determine a hue difference of $-180°$ to $+180°$.

Figure 32:
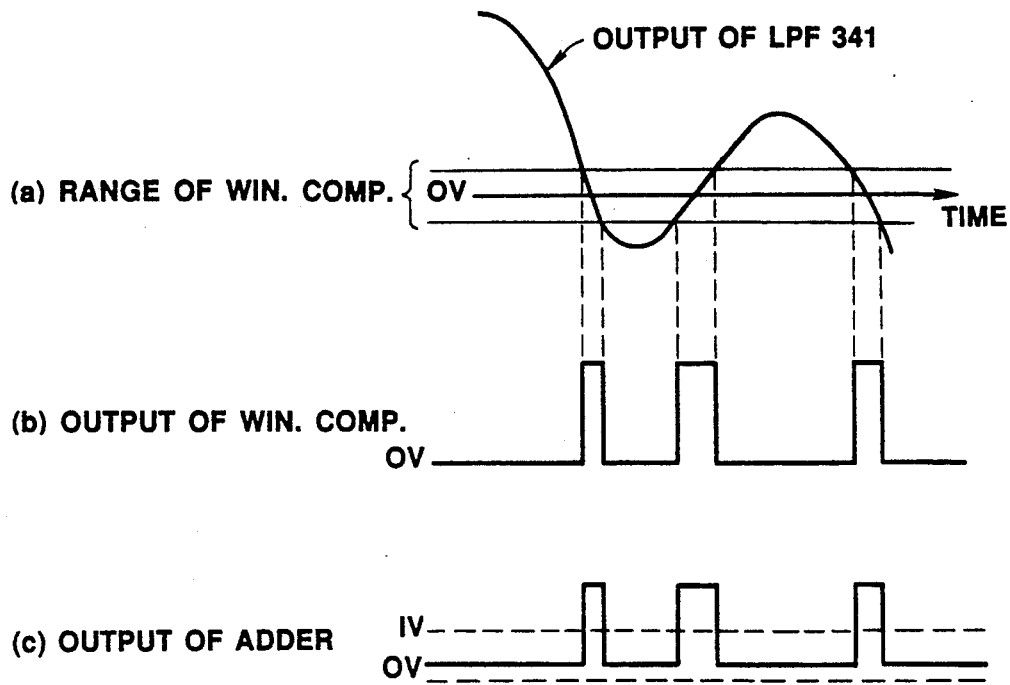
FIG. 32 is an operation explaining view of a window comparator.

The output of the above mentioned comparator 337 will elevate the output of a flip-flop 338 to a high level at the time of the rise of a signal applied to the setting terminal of the flip-flop 338. The output of the comparator 336 is applied to the resetting terminal of the flip-flop 338 and will lower the output of the flip-flop to a low level at the time of the rise of the signal. The output of the flip-flop 338 is of a square wave having a pulse width corresponding to $\phi_A - (\phi_M - 180°)$ as shown in FIG. 31f, is sliced into fixed amplitudes, is then passed through a low pass filter 341 and is converted to a voltage signal proportional in the pulse width to $\phi_A - (\phi_M - 180°)$. Here, the pulse width is sliced into fixed amplitudes by the slicing circuit 339, because the slicing circuit can be formed of a differential amplifier and a circuit stable in the temperature can be obtained. Now, the output of the low pass filter is $\phi_A - (\phi_M - 180°) = \phi_A - \phi_M = 180°$ and therefore the direct current voltage part corresponding to 180° is subtracted by a subtracter 342 to leave a voltage corresponding to $\phi_A - \phi_M$. The output of this subtracter 342 is input into a window comparator 343 and a process shown in FIG. 32 is made.

When the level to be compared with the output $\phi_A - \phi_M$ of the low pass filter 341 passed through the subtracter 342 is set near the 0 level as shown in FIG. 32a and the value of $\phi_A - \phi_M$ is in the range, the window comparator 343 will output a pulse as shown in FIG. 32b. This pulse is divided by a variable resistance 344, further a potential V having a voltage source 345 is added, the voltage Vr of a variable voltage source 347 is simplified by an adder 346, the direct current level of the signal is adjusted and the signal is input into multipliers 348 and 349 forming the chroma enhancing circuit 243.

The signals input into the above mentioned respective multipliers 348 and 349 are multiplied by the input color difference signals $R-Y$ and $B-Y$ and enhanced signals $(R-Y)'$ and $(B-Y)'$ are output from this chroma enhanced color 342.

The output of the above mentioned adder 346 is as shown in FIG. 31c. Therefore, in case there is no hue difference from the color to be enhanced by the multipliers 348 and 349, a voltage of 1 V or more will be multiplied and, in case there is a hue difference from the color to be enhanced, a voltage of 1 V or less will be multiplied to reduce the chroma. Here, the signal to be multiplied by the multipliers 348 and 349 is made a pulse but the high frequency component of the waveform may be cut with a low pass filter or the like so that the waveform may be of a normal distribution form or any other form. This waveform is determined mostly by experiences.

By this color enhancing circuit 241, the chroma of any color can be raised and the chroma of the other color can be reduced. Only a fixed color can be relieved to be recognized and enhanced.

Figure 33:
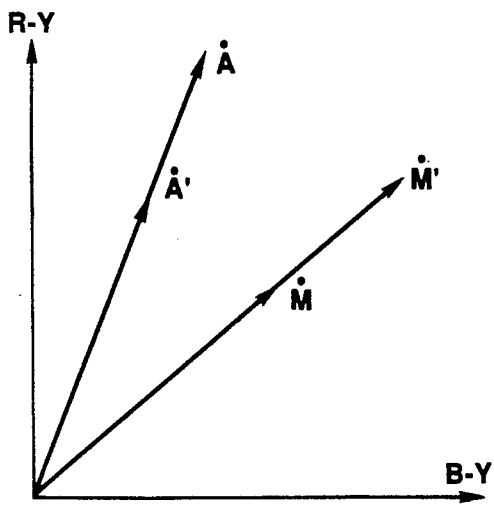
FIG. 33 is an explanatory view showing the manner of enhancing a color by a color enhancing circuit.

In the color vector coordinates shown in FIG. 33 by the color difference signals $R-Y$ and $B-Y$ when passed through the above mentioned color enhancing circuit 241, the color vector of the color not to be made conspicuous is made M and one of the color vectors forming the picture image is made A. When passed through this color enhancing circuit 241, the color signal near the color vector M will be enhanced in the chroma to be as in M' but the color vector A of the hue difference deviated from this color vector M will be reduced in the chroma to be as in A'. The picture image part near the color vector M to be made conspicuous can be enhanced by this operation. Therefore, if the above mentioned color vector M not to be made conspicuous is set to be a hue near the affected part rather than the hue of the normal part, for example, within a body cavity, in case an affected part or the like slightly deviated from the hue of the normal part exists, the affected part will be able to be relieved.

The color enhancing circuit 241 in this seventh embodiment can be applied also to FIGS. 19, 20 and 21.

The adders 27, 28 and 29 for compositing the parent picture surface and child picture surface can be formed of such selecting (changing) means as a switch changing the parent picture surface and child picture surface.

Figure 34A:
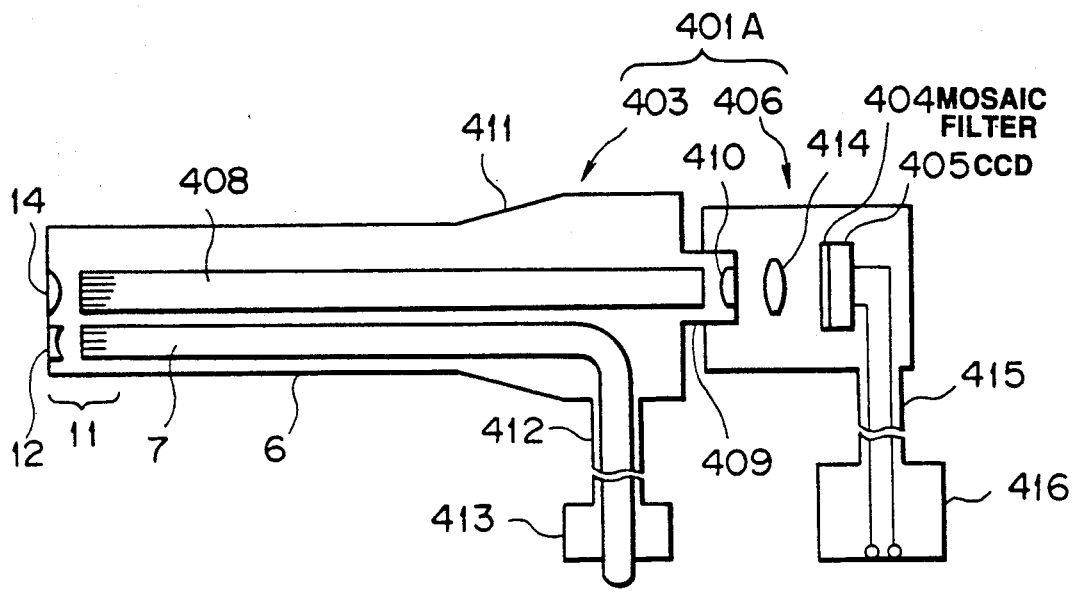
FIG. 34 is a formation view of a television camera externally fitted scope which can be used instead of an electronic scope.
Figure 34B:
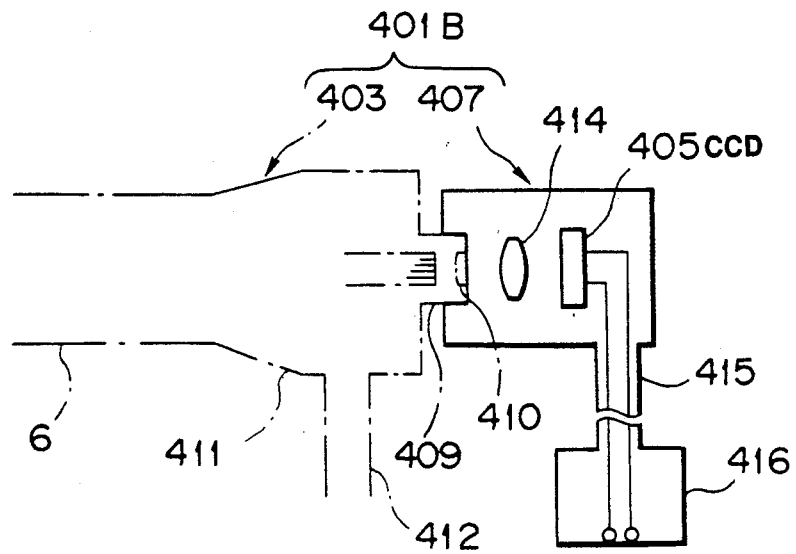

In the above described respective embodiments, television camera externally fitted scopes 401A and 401B as are shown in FIGS. 34A and B can be used instead of the electronic endoscopes 2 and 2'.

The television camera externally fitted scope 401A is fitted with a television camera 406 having a built-in CCD 405 fitted with a mosaic filter 404 in a fiber scope 403.

The other television camera externally fitted scope 401B is fitted with a television camera 407 having a built-in CCD having no mosaic filter 404.

In the above mentioned fiber scope 403, in the electronic scope 2 or 2', one end of the image guide 408 formed of a fiber bundle is arranged in the focal plane of the objective lens 14 and an optical image is transmitted to the other end on the eyepiece part 409 side.

In this eyepiece part 409, an eyepiece lens 410 is arranged so that the transmitted optical image may be magnified and observed. (The electronic scope 2 or 2' has no eyepiece part 410.)

In this fiber scope 403, the light guide cable 412 is extended from the operating part 411 and the connector 113 at the end is connected to the light source apparatus 3 or 3' to feed a white color light or frame sequential light.

The others are of the same formations as in the electronic scope 2 or 2' and the same reference numerals are attached to the same components.

The television camera 406 or 407 can be fitted to the above mentioned eyepiece part 409.

Each television camera 406 or 407 has an image forming lens and can form an image of the CCD 405.

The signal cable 115 is extended from each television camera 406 or 407 and the connector 116 at the end can be connected to the video image signal processing circuit 4 or 4'.

A different embodiment can be formed by combining the above described respective embodiments.

What is claimed is:

1. An electronic endoscope apparatus comprising:
an electronic endoscope including
an elongate insertable part,
an objective optical system provided on a tip side of said insertable part,
an imaging device photoelectrically converting an optical image based on said objective optical system into a picture image signal, and
a light emitting means for emitting an illuminating light from the tip side of said insertable part;
a driving means for outputting a driving signal for reading out the picture image signal photoelectrically converted by said imaging device;
a signal processing means for producing a standard video signal by processing said picture image signal, said signal processing means provided with
a first signal processing means for processing a first picture image signal which reproduces an original picture image,
a second signal processing means for processing a second picture image signal corresponding to a special picture image, to which additional image processing is done, which is different from the original picture image, and
a mixing means for mixing said first and second picture image signals; and
a displaying means for simultaneously displaying said first picture image signal and second picture image signal processed by said signal processing means.

2. An electronic endoscope apparatus according to claim 1 wherein said electronic endoscope is an electronic scope in which said imaging device is arranged in a focal plane of said objective optical system.

3. An electronic endoscope apparatus according to claim 1 wherein said electronic endoscope is a television camera externally fitted scope formed of a fiber scope provided with an image guide transmitting an optical image by said objective optical system and a television camera fittable to an eyepiece part of said fiber scope and having said imaging device built-in.

4. An electronic endoscope apparatus according to any one of claims 1, 2 and 3 wherein said imaging device has a color separating filter fitted in front of an imaging surface.

5. An electronic endoscope apparatus according to any one of claims 1, 2 and 3 wherein said imaging device does not have a color separating filter arranged in front of an imaging surface.

6. An electronic endoscope apparatus according to claim 4 wherein said light emitting means emits a white color light.

7. An electronic endoscope apparatus according to claim 5 wherein said light emitting means sequentially emits light in wavelength ranges different from each other.

8. An electronic endoscope apparatus according to claim 6 wherein said light emitting means is a light guide transmitting an illuminating light fed to one end and emitting light from the other end surface arranged on the tip side of said insertable part.

9. An electronic endoscope apparatus according to any one of claims 1, 2 and 3 wherein at least one of said first and second signal processing means has a picture image memory.

10. An electronic endoscope apparatus according to claim 9 wherein said picture image memory is controlled in reading out the picture image signals output respectively from said first and second signal processing means so as to be separated.

11. An electronic endoscope apparatus according to any one of claims 1, 2 and 3 wherein said second signal processing means has a differential circuit for outputting a differential signal.

12. An electronic endoscope apparatus according to any one of claims 1, 2 and 3 wherein said second signal processing means has an outline enhancing circuit outputting an outline enhancing signal.

13. An electronic endoscope apparatus according to claim 12 wherein said outline enhancing circuit has a means for selectively outputting primary and secondary outline enhancing signals.

14. An electronic endoscope apparatus according to any one of claims 1, 2 and 3 wherein said first signal processing means has a child picture surface displaying memory for displaying a child picture surface as contracted to be smaller than said special picture image.

15. An electronic endoscope apparatus according to any one of claims 1, 2 and 3 wherein said second signal processing means has a color enhancing circuit enhancing a vicinity of a designated color.

16. An electronic endoscope apparatus according to any one of claims 1, 2 and 3 wherein said second signal processing means has a specific frequency extracting circuit extracting only a signal component of a specific frequency band.

17. An electronic endoscope apparatus according to any one of claims 1, 2 and 3 wherein said second signal processing means is a difference processing circuit processing a difference between picture image components imaged respectively in different wavelength bands.

18. An electronic endoscope apparatus according to any one of claims 1, 2 and 3 wherein said second signal processing means is a division processing circuit division-processing between picture image signal components imaged respectively in different wavelength bands.

19. An electronic endoscope apparatus according to any one of claims 1, 2 and 3 wherein said displaying means simultaneously displays said special picture image and an original picture image contracted to be smaller than a size of said special picture image.

20. An electronic endoscope apparatus according to any one of claims 1, 2 and 3 wherein said displaying means simultaneously displays said special picture image and an original picture image cut on both sides in a horizontal direction as compared with a size of said special picture image.

21. A signal processing apparatus comprising:
a first signal processing means for processing a first picture image signal to reproduce an original picture image;
a second signal processing means for producing a second picture image signal corresponding to a special picture image which is different from said original picture image and to which additional image processing is done on said first picture image signal; and
a mixing means for mixing said first and second picture image signals,
wherein said original picture image and special picture image are simultaneously displayed in a displaying means using the picture image signals mixed by said mixing means.

22. A signal processing apparatus according to claim 21 further comprising an encoder converting an output signal of said mixing means into a standard video signal.

23. A signal processing apparatus according to claim 21 or 22 wherein at least one of said first and second signal processing means has a picture image memory.

24. A signal processing apparatus according to claim 23 wherein said picture image memory is controlled in reading out picture image signals so that the picture image signals output respectively from said first and second signal processing means may be separated.

25. A signal processing apparatus according to any one of claims 21, or 22 wherein said second signal processing means has a differential circuit outputting a differential signal.

26. A signal processing apparatus according to any one of claims 21, or 22 wherein said second signal processing means has an outline enhancing circuit outputting an outline enhancing signal.

27. A signal processing apparatus according to claim 26 wherein said outline enhancing circuit can selectively output primary and secondary outline enhancing signals.

28. A signal processing apparatus according to claim 23 wherein said first signal processing means has a child picture surface displaying memory displaying a child picture surface as contracted.

29. A signal processing apparatus according to claim 21 wherein said second signal processing means has a color enhancing circuit enhancing a vicinity of a designated color.

30. A signal processing apparatus according to claim 21 wherein said second signal processing means has a specific frequency extracting circuit extracting a signal component of a specific frequency band.

31. A signal processing apparatus according to claim 21 wherein said second signal processing means is a difference processing circuit difference processing between picture image signal components imaged respectively in different wavelength bands.

32. A signal processing apparatus according to claim 21 wherein said second signal processing means is a division processing circuit division processing between picture image signal components imaged respectively in different wavelength bands.

33. A signal processing apparatus according to claim 25 having a first coefficient varying means for varying an amplitude of said differential signal.

34. A signal processing apparatus according to claim 25 wherein said second signal processing means has an adding means of a picture image signal not differentiated by said differential signal.

35. A signal processing apparatus according to claim 34 having a second coefficient varying means for varying an amplitude of said picture image signal not differentiated.

36. A signal processing apparatus according to claim 35 having a for changing means changing a coefficient of first/second coefficient varying means.

37. A signal processing apparatus according to claim 25 wherein said differential circuit can selectively output a primary differential signal and secondary differential signal.

38. A signal processing apparatus according to claim 33 wherein said second signal processing means has a for level shifting means level shifting a signal not differentiated.

39. A signal processing apparatus according to claim 38 further having a level shift amount change setting means of said level shifting means.

40. A signal processing apparatus according to claim 21 wherein said first and second signal processing means have a common signal processing part and can be changed to be of different signal processing characteristics by a change by a changing means synchronized with a horizontal synchronizing signal.

41. A signal processing apparatus according to claim 40 which is set by changing said changing means at a first signal processing characteristic reproducing an original picture image and a second signal processing characteristic producing a special picture image different in outline/structure from the original picture image.

42. A signal processing apparatus according to claim 41 wherein said second signal processing characteristic can output respective differential signals of a primary differential and secondary differential by a mode changing means.

43. A signal processing apparatus according to claim 42 having a means of varying an amplitude of said differential signal.

44. A signal processing apparatus according to claim 43 wherein said second signal processing means has a level shifting means for a signal not differentiated.

45. A signal processing apparatus according to claim 44 wherein said second signal processing means has an adding means of said differential signal and a signal not differentiated.

46. A signal processing apparatus according to claim 45 having an amplitude varying means for said signal not differentiated.

* * * * *